US008133700B2

(12) United States Patent
Slobedman et al.

(10) Patent No.: US 8,133,700 B2
(45) Date of Patent: Mar. 13, 2012

(54) LATENT PHASE VIRAL INTERLEUKIN-10-(VII-10) AND USES THEREOF

(75) Inventors: Barry Slobedman, New South Wales (AU); Allison Denise Abendroth, New South Wales (AU); Christina Anne Jenkins, New South Wales (AU)

(73) Assignee: The University of Sydney, Sydney, New South Wales (AU)

( * ) Notice: Subject to any disclaimer, the term of this patent is extended or adjusted under 35 U.S.C. 154(b) by 872 days.

(21) Appl. No.: 10/580,922

(22) PCT Filed: Nov. 26, 2004

(86) PCT No.: PCT/AU2004/001675
§ 371 (c)(1),
(2), (4) Date: Mar. 15, 2007

(87) PCT Pub. No.: WO2005/052159
PCT Pub. Date: Jun. 9, 2005

(65) Prior Publication Data
US 2009/0214463 A1    Aug. 27, 2009

(30) Foreign Application Priority Data

Nov. 28, 2003  (AU) ................................ 2003906613

(51) Int. Cl.
*C12N 15/24*  (2006.01)
*C12N 15/38*  (2006.01)
*C12Q 1/68*   (2006.01)
(52) U.S. Cl. ................. 435/69.52; 424/85.2; 424/229.1; 435/91.4; 514/4.2
(58) Field of Classification Search .................. None
See application file for complete search history.

(56) References Cited

U.S. PATENT DOCUMENTS 7,361,460 B2 * 4/2008 Williams et al. .............. 435/6
7,407,744 B2 * 8/2008 Liu et al. ..................... 435/5

FOREIGN PATENT DOCUMENTS

| WO | WO 01/16153 A1 | 3/2001 |
| WO | WO 02/057437 A2 | 7/2002 |
| WO | WO 02/077267 A2 | 10/2002 |

OTHER PUBLICATIONS

Anti-Viral HCMV IL-10 Antibody Product Data Sheet, R&D Systems Inc.
Beisser, P.S. et al. 2001 "Human Cytomegalovirus Chemokine Receptor Gene US28 is Transcribed in Latently Infected THP-1 Monocytes." *Journal of Virology*, 75:5949-5957.
Bevan IS et al. 1993 "Detection of human cytomegalovirus DNA in peripheral blood leukocytes by the polymerase chain reaction" *Transfusion* 33:783-784.
Biotinylated Anti-Viral HCMV IL-10 Antibody Product Data Sheet, R&D Systems Inc.
Bitsch, A. et al. 1992 "Failure to detect human cytomegalovirus DNA in peripheral blood leukocytes of healthy blood donors by the polymerase chain reaction"*Transfusion* 32:612-617.
Chee MS et al. 1990 "Analysis of the protein-coding content of the sequence of human cytomegalovirus strain AD169." *Curr Top Microbiol Immunol.* 154:125-169.
Chevalier Mathieu S. et al. 2002 "Binding of Human Cytomegalovirus US2 to Major Histocompatibility Complex Class I and II Proteins is Not Sufficient for Their Degradatbn." *Journal of Virology* 76:8265-8275.
Database EMBL online XP002431771 (Lockridge et al.).
Database EMBL online XP002431778 (Kotenko et al.).
Database Geneseq online XP002431780 (Pestka and Kotenko).
Database Uniprot online XP002431779.
Goodrum Felicia D. et al .2002 "Human cytomegalovirus gene expression during infection of primary hematopoietic progenitor cells: A model for latency." *Proc Natl Acad Sci USA* 99:16255-16260.
Hahn G. et al. 1998 Cytomegalovirus remains latent in a common precursor of dendritic and myeloid cells. *Proc Natl Acad Sci USA* 95:3937-3942.
Hegde, N.R. et al. 2002 "Inhibition of HLA-DR Assembly, Transport, and Loading by Human Cytomegalovirus Glycoprotein US3: a Novel Mechanism for Evading Major Histocompatibility Complex Class II Antigen Presentation." *Journal of Virology* 76:10929-10941.
Hsu DH et al. 1990 "Expression of interleukin-10 activity by Epstein-Barr virus protein BCRF-1." *Science* 250:830-832.
Jenkins C. et al. "Human cytomegalovirus UL111.5A-region transcripts are expressed during both experimental and natural latent infection of myeloid cells"3rd College of Health Sciences and Medical Foundation Research Conference: From Cell to Society 3, Sep. 18, 2002 to Sep. 19, 2002 Blue Mountains Australia, mini-poster No. 22-9.
Jenkins C. et al. 2004 "A Novel Viral Transcript with Homology to Human Interleukin.10 is Expressed During Latent Human Cytomegalovirus Infection." *Journal of Virology* 78:1440-1447.
Jones B.C. et al. 2002 "Crystal structure of human cytomegalovirus IL-10 bound to soluble human IL-10R1." *Proc Natl Acad Sci USA* 99:9404-9409.
Just M et al. 1975 "Immunisation trials with live attenuated cytomegalovirus TOWNE 125." *Infection* 3:111-114.
Kondo K and Mocarski. ES 1995"Cytomegalovirus latency and latency-specific transcription in hematopoietic progenitors." *Scan J Infect Dis Suppl* 99:63-67.

(Continued)

*Primary Examiner* — Elly-Gerald Stoica
(74) *Attorney, Agent, or Firm* — Knobbe Martens Olson & Bear LLP

(57) ABSTRACT

The present invention relates to a purified nucleic acid sequence encoding a homologue of human interleukin 10 (IL-10), wherein said IL-10 homologue is expressed during the latent phase of infection by a virus of the herpesvirideae group. The present invention also relates to uses of this polypeptide, in particular for diagnosing disease states and screening for modulator and inhibitor compounds of such polypeptides and in turn the virus itself, screening for infection in vertebrates and biological tissue, cleansing of infected biological tissues, and in the treatment and/or prophylaxis and/or diagnosis of disease caused by a virus of the herpesvirideae group.

11 Claims, 7 Drawing Sheets

OTHER PUBLICATIONS

Kondo Kazuhiro et al. 1994 "Human Cytomegalovirus latent infection of granulocyte macrophage progenitors." *Proc Natl Acad Sci USA* 91:11870-11883.

Kotenko, S.V. et al. 2000 "Human cytomegalovirus harbors its own unique IL-10 homolog (CMVIL-10)" *Proc Natl Acad Sci USA* 97:1695-1700.

Landini MP et al. 2000 "Humoral immune response to proteins of human cytomegalovirus latency-associated transcripts." *Biol Blood Marrow Transplant* 6:100-108.

Larsson S et al. 1998 "Cytomegalovirus DNA can be detected in peripheral blood mononuclear cells from all seropositive and most seronegative healthy blood donors over time." *Transfusion* 38:271-278.

Lockridge Kirsten M. et al. 2000 "Primate Cytomegaloviruses Encode and Express an IL-10-like Protein." *Virology* 268:272-280.

Mendelson M et al. 1996 "Detection of endogenous human cytomegalovirus in CD34+ bone marrow progenitors." *J Gen Virol* 77:3099-3102.

Miyazaki Isao et al. 1993 "Viral Interleukin 10 is Critical for the Induction of B Cell Growth Transformation by Epstein-Barr Virus." *J. Exp Medicine* 187:439-447.

Moore K. W. et al. 2001 "Interleukin-10 and the Interleukin-10 receptor." *Annu Rev Immunol* 19:683-765.

Moore KW et al. 1990 "Homology of cytokine synthesis inhibitory factor (IL-10) to the Epstein-Barr virus gene BCRFI." *Science* 248:1230-1234.

Plotkin S. A. et al. 1975 "Candidate Cytomegalovirus Strain for Human Vaccination." *Infection and Immunity* 12:521-527.

Quinnan GV Jr. et al. 1984 "Comparative virulence and immunogenicity of the Towne strain and a nonattenuated strain of cytomegalovirus" *Ann Intern Med* 101:478-483.

Rawlinson W. D.and Barrell B. G. 1993 "Spliced Transcripts of Human Cytomegalovirus." *Journal of Virology* 6:5502-5513.

Redpath, S et al. 2001 "Hijacking and exploitation of IL-10 by intracellular pathogens." *Trends in Microbiology* 9:86-92.

Rode HJ et al. 1993 "The genome of equine herpesvirus type 2 harbors an interleukin 10 (IL10)like gene." *Virus Gene.* 7:111-116.

Slobedman B. et al. 1999 "Quantative Analysis of Latent Human Cytomegalovirus." *Journal of Virology* 73:4806-4812.

Slobedman B. et al. 2002 "Latent cytomegalovirus down-regulates major histocompatibility complex class II expression on myeloid progenitors." *Blood* 100:2867-2873.

Smith KL et al. 1993 "Detection of cytomegalovirus in blood donors by the polymerase chain reaction." *Transfusion* 33:497-503.

Söderberg-Nauclér et al. 1997 "Reactivation of Latent Human Cytomegalovirus by Allogeneic Stimulation of Blood Cells from Healthy Donors" *Cell* 91:119-126.

Spencer J.V. et al. 2002 "Potent immunosuppressive Activities of Cytomegalovirus-Encoded Interleukin-10" *Journal of Virology* 76:1285-1292.

Taniguchi M. et al. 1996 "Essential requirement of an invariant Vα14 T cell antigen receptor expression in the development of natural killer T cells" *Proc Natl Acad Sci USA* 93:11025-11028.

Taylor-Weideman, J. et al. 1991 "Monocytes are a major site of persistence of human cytomegalovirus in peripheral blood mononuclear cells" *Journal of General Virology* 72:2059-2064.

Tomazin, R. et al. 1999 "Cytomegalovirus US2 destroys two components of the MHC class II pathway, preventing recognition by CD4+ T cells" *Nature Medicine* 5:1039-1043.

White K.L. et al. 2000 "Human Cytomegalovirus Latency-Associated Protein in pORF94 is Dispensable for Productive and Latent Infection" *Journal of Virology* 74: 9333-9337.

Xu Z-G et al. 2001 "The latency patter of Epsein-Barr virus infection and viral IL-10 expression in cutaneous natural killer/T-cell lymphomas." *British Journal of Cancer* 84:920-925.

\* cited by examiner

LATENT PHASE VIRAL INTERLEUKIN-10-(VII-10) AND USES THEREOF

This application is U.S. National Phase of International Application PCT/AU2004/001675, filed Nov. 26, 2004 designating the U.S., and published in English as WO 2005/052159 on Jun. 9, 2005, which claims priority to Australian Patent No. 2003906613, filed Nov. 28, 2003, both of which are hereby expressly incorporated by reference in their entireties.

TECHNICAL FIELD

The present invention relates to a homologue of human interleukin 10 (IL-10) expressed during latent phase of infection by a virus of the herpesvirideae group. The present invention also relates to uses of this polypeptide, in particular for diagnosing disease states and screening for modulator and inhibitor compounds of such polypeptides and in turn the virus itself, screening for infection in vertebrates and biological tissue, cleansing of infected biological tissues, and in the treatment and/or prophylaxis and/or diagnosis of disease caused by a virus of the herpesvirideae group.

BACKGROUND OF THE INVENTION

Human cytomegalovirus (CMV) is a virus of the herpesvirideae group and a species-specific β-herpesvirus that causes severe disease in neonates and in immunosuppressed individuals such as allograft transplant recipients and those with AIDS. In common with all herpesviruses, the life cycle of CMV is characterized by productive, latent and reactivation phases. During productive infection, viral genes are expressed in a temporarily regulated cascade resulting in the synthesis of new, infectious virus. At some point after initial infection, the virus establishes a life-long latent infection in myeloid lineage cells during which time viral gene expression is restricted and infectious virus is not produced. Periodically, virus can reactivate from latency, a process that results in the generation of infectious virus and which is the major cause of serious CMV associated diseases common in recipients of solid organ and bone marrow allografts. Other members of the herpesviridae group are also able to reactivate a latent state to cause clinical disease. The ability of CMV and other members of the herpesviridae family to persist in a latent state for the life of the host ensures a reservoir of virus for subsequent reactivation and highlights the importance of latency to the success of this virus as a human pathogen.

Attempts to understand the molecular basis of latency of viruses of the herpesvirideae group, such as CMV latency, have included studies to identify and characterize the function(s) of viral genes expressed during latent infection of myeloid progenitor cells. Studies utilizing cultured granulocyte-macrophage progenitors (GM-Ps) in an experimental model of latency identified two classes of CMV latency associated transcripts (CLTs), denoted sense and antisense CLTs, which originate from the major immediate early (MIE) region of the viral genome (3, 7-9, 19). However, the functions of the MIE region CLTs have not yet been defined. Furthermore, few studies have sought to assess viral gene expression during latency.

The present invention relates to the surprising discovery that a region of the genome of a virus of the herpesvirideae group is expressed during the latent phase of infection.

SUMMARY OF THE INVENTION

According to a first embodiment of the present invention there is provided a purified nucleic acid sequence encoding a homologue of human interleukin 10 (IL-10), wherein said IL-10 homologue is expressed during the latent phase of infection by a virus of the herpesvirideae group.

The nucleic acid sequence may be as set forth in SEQ ID NO:1, or a fragment or variant thereof.

According to a second embodiment of the present invention there is provided a human interleukin 10 (IL-10) homologue polypeptide, wherein said IL-10 homologue is expressed during the latent phase of infection by a virus of the herpesvirideae group. The IL-10 homologue may be encoded by the nucleic acid sequence in accordance with the first embodiment of the invention. The IL-10 homologue may be the product of alternative splicing of the primary RNA transcript. For example, the IL-10 homologue may be from the UL111.15A region of the cytomegalovirus genome. The IL-10 homologue may have the amino acid sequence as set forth in SEQ ID NO:10, or the amino acid sequence as set forth in SEQ ID NO:10 including one or more conservative amino acid substitutions.

The virus of the herpesvirideae group may be selected from the group consisting of: Epstein-Barr virus, human herpesvirus (HHV)-6, HHV-7, HHV-8, varicella zoster virus, herpes simplex type 1 and type 2 virus and cytomegalovirus. Moreover, the virus may be cytomegalovirus.

In a third embodiment, the present invention provides a vector comprising a nucleic acid sequence in accordance with the first embodiment of the invention.

In a fourth embodiment, the present invention provides a recombinant host cell comprising the nucleic acid in accordance with the first embodiment of the invention or the vector in accordance with the third embodiment of the invention.

In a fifth embodiment, the present invention provides a recombinant host cell capable of expressing the polypeptide or variant or fragment thereof of the second embodiment of the invention.

In a sixth embodiment, the present invention provides an isolated ligand that selectively binds to the polypeptide of the second embodiment of the invention. For example, the isolated ligand may be an antibody or fragment thereof.

In a seventh embodiment, the present invention provides a method of identifying a compound that interacts with the polypeptide of the second embodiment of the invention, the method comprising the steps of:
(a) contacting a candidate compound with the polypeptide under conditions suitable to permit interaction of the candidate compound to the polypeptide; and
(b) detecting the interaction between said candidate compound and the polypeptide.

The detection of the interaction may comprise adding a labelled substrate and measuring a change in the labelled substrate.

According to an eighth embodiment of the present invention there is provided a method of identifying a compound that binds to the polypeptide of the second embodiment, the method comprising the steps of:
(a) contacting a candidate compound with the polypeptide; and
(b) assaying for the formation of a complex between the candidate compound and the polypeptide.

The assay for the formation of a complex may be selected from the group consisting of a competitive binding assay, a two-hybrid assay and an immunoprecipitation assay.

According to a ninth embodiment of the present invention there is provided a method of screening for a compound that modulates the activity of the polypeptide of the second embodiment, the method comprising the steps of:

(a) contacting the polypeptide with a candidate compound under conditions suitable to enable interaction of the candidate compound to the polypeptide; and
(b) assaying for activity of the polypeptide.

Assaying for activity of the polypeptide may comprise adding a labelled substrate and measuring a change in the labelled substrate. The modulation of activity may be as a result of an inhibition of activity of the polypeptide.

According to a tenth embodiment of the present invention there is provided a method of diagnosing a disease state, or predisposition to a disease state, in a subject, the method comprising the steps of:
(a) obtaining a biological sample from the subject; and
(b) assaying for expression of the polypeptide of the second embodiment.

Assaying for the expression of the polypeptide thereof may comprise contacting the biological sample with a compound capable of interacting with the polypeptide such that the interaction can be detected. The compound capable of selectively interacting with the polypeptide or variant or fragment thereof may be an antibody or fragment thereof to the human IL-10 homologue, wherein said IL-10 homologue is expressed during the latent phase of infection by a virus of the herpesvirideae group.

According to an eleventh embodiment of the present invention there is provided a method of identifying an agent which is an inhibitor of infection by a virus of the herpesvirideae group, the method comprising contacting a cell or cell extract with one or more candidate agents, determining whether there is a change in the activity of the polypeptide of the second embodiment, and thereby determining whether the agent is an inhibitor of a virus of the herpesvirideae group.

The viruses of the herpesvirideae group may be selected from the group consisting of: Epstein-Barr virus, human herpesvirus (HHV)-6, HHV-7, HHV-8, varicella zoster virus, herpes simplex type 1 and type 2 and cytomegalovirus.

According to a twelfth embodiment of the present invention there is provided a method of identifying an agent suitable for use in the treatment or prevention of a disease state in a subject, the method comprising:
(a) obtaining a biological sample from the subject,
(b) contacting the sample with a candidate agent,
(c) determining whether there is a change in the activity of the polypeptide of the second embodiment, and
(d) thereby determining whether the agent is suitable for use in the treatment of the disease state.

In a thirteenth embodiment the present invention provides compounds identified by the methods of the seventh, eighth, ninth, eleventh and twelfth embodiments.

In a fourteenth embodiment the present invention provides a method for treating or preventing a disease state in a subject, the method comprising administering to the subject a therapeutically effective amount of the ligand of the sixth embodiment or a compound identified by the method of any one of the seventh, eighth, ninth, eleventh and twelfth embodiments.

According to a fifteenth embodiment of the present invention there is provided a kit comprising the polypeptide of the second embodiment or the nucleic acid in accordance with the first embodiment of the invention. Alternatively, or in addition, the kit may contain a ligand or fragment thereof of the sixth embodiment, wherein the ligand may be in the form of an antibody or fragment thereof.

The kit may be used for carrying out the methods of the seventh to the fourteenth embodiments above, or the methods of sixteenth to twenty-seventh embodiments set out below.

According to a sixteenth embodiment of the present invention there is provided a method for screening a subject for infection by a virus of the herpesvirideae group, the method comprising:
(a) obtaining a biological sample from said subject;
(b) contacting said sample with the ligand of the sixth embodiment, and
(c) detecting the presence of the ligand selectively bound to the polypeptide of the second embodiment.

The sample within which the method of screening is performed may be a plasma, nucleic acid or cell sample.

According to a seventeenth embodiment of the present invention there is provided a method for screening a subject for infection by a virus of the herpesvirideae group, the method comprising:
(a) obtaining a biological sample from said subject;
(b) contacting said biological sample from said subject with the nucleic acid sequence of the first embodiment; and
(c) detecting the presence or absence of hybridisation between the nucleic acid of said biological sample and the nucleic acid sequence of the first embodiment.

According to an eighteenth embodiment of the present invention there is provided a method for screening a biological sample for infection by a virus of the herpesvirideae group, the method comprising:
(a) contacting said biological sample with the nucleic acid sequence of the first embodiment; and
(b) detecting the presence or absence of hybridisation between the nucleic acid sample of said biological sample and the nucleic acid sequence of the first embodiment.

In the methods of the seventeenth or eighteenth embodiments, the nucleic acid sequence of the first embodiment corresponds to a region of the nucleic acid sequence which is capable of selectively hybridising to the nucleic acid encoding the IL-10 homologue expressed during the latent phase of infection by a virus of the herpesvirideae group. More typically, the region of the nucleic acid sequence of the first embodiment corresponds to a region encoding polypeptide/peptide fragments of the C-terminal of the IL-10 homologue. The region may correspond to any one of SEQ ID NOS: 2 to 9. For instance, oligonucleotides as set out in SEQ ID NOS 2-8 may be used as primers in a PCR reaction useful in the screening processes of the seventeenth or eighteenth embodiments of the invention. Further, SEQ ID NO:9 may be used as a nucleic acid probe in accordance with the screening processes of the seventeenth or eighteenth embodiments of the invention.

The hybridisation may occur and be detected through techniques that are standard and routine amongst those skilled in the art, and include southern and northern hybridisation, polymerase chain reaction (PCR) and ligase chain reaction (LCR).

According to a nineteenth embodiment of the present invention there is provided a method for screening a biological sample for infection by a virus of the herpesvirideae group, the method comprising:
(a) contacting said biological sample with the ligand of the sixth embodiment, and
(b) detecting the presence of the ligand selectively bound to the polypeptide of the second embodiment.

The sample within which the methods of any one of the tenth through to nineteenth embodiment is performed may be a sample selected from the group consisting of: blood, bone marrow or organ(s) or spinal fluid. The sample within which the method of screening is performed may be intended to be used in a subject selected from the group consisting of: transplant recipients (for example, proposed recipients of bone marrow, stem cell or solid organ transplants), subjects undergoing immunosuppression therapy and immunocompromised subjects. The immunocompromised subject may be a subject suffering from acquired immune deficiency syndrome (AIDS) or diagnosed as infected with human immunodeficiency virus (HIV).

According to a twentieth embodiment of the present invention there is provided a method of immunosuppression in a subject, said method comprising administering a therapeutically effective amount of the polypeptide of the second embodiment.

In relation to any one of the tenth through to twentieth embodiments of the invention, the viruses of the herpesvirideae group may be those selected from the group consisting of: Epstein-Barr virus, human herpesvirus (HHV)-6, HHV-7, HHV-8, varicella zoster virus, herpes simplex type 1 and type 2 and cytomegalovirus.

According to a twenty-first embodiment of the invention, there is provided a vaccine, wherein said vaccine comprises a nucleic acid molecule as defined in accordance with the first embodiment of the invention, or a polypeptide as defined in accordance with the second embodiment of the invention, or a ligand as defined in accordance with the sixth embodiment of the invention, together with a pharmaceutically acceptable carrier, adjuvant and/or diluent.

The vaccine may be administered in the form of a DNA based vaccine, and the means of administration includes the so-called "gene-gun".

Typically, the vaccine is formulated for administration via an oral, inhalation, topical or parenteral route. More typically, the route of administration is parenteral.

According to a twenty-second embodiment of the invention, there is provided a method for inducing an immune response in a subject against disease associated with infection by a virus of the herpesvirideae group, comprising administering to said vertebrate an immunologically effective amount of the polypeptide as defined in accordance with the second embodiment of the invention, or a ligand as defined in accordance with the sixth embodiment of the invention, or a vaccine as defined in accordance with the twenty-first embodiment of the invention.

According to a twenty-third embodiment of the invention, there is provided a method for the treatment and/or prophylaxis of disease associated with infection by a virus of the herpesvirideae group in a subject, wherein said method comprises administering a therapeutically effective amount of the polypeptide as defined in accordance with the second embodiment of the invention, or a ligand as defined in accordance with the sixth embodiment of the invention, or a vaccine as defined in accordance with the twenty-first embodiment of the invention.

The polypeptide or ligand may be administered together with a pharmaceutically acceptable carrier, adjuvant and/or diluent. Similarly, the polypeptide or ligand as administered may also be simultaneously or sequentially administered with one or more therapeutically effective compounds, such as one or more cytokines.

According to a twenty-fourth embodiment of the invention, there is provided a method of cleansing a biological sample of infection by a virus of the herpesvirideae group, the method comprising:
  (a) contacting said biological sample with a ligand of the sixth embodiment,
  (b) detecting the presence of the ligand bound to a cell expressing the polypeptide of the second embodiment, and
  (c) removing said cells to which said ligand binds.

The sample within which the method of screening is performed may be any sample intended for transplantation, for example, a sample selected from the group consisting of: blood, bone marrow or organ(s) and spinal fluid.

The assay used in the twenty-fourth embodiment may comprise an intracellular staining assay with the ligand, wherein the cells identified are then removed from a mixed cell population by, for example, flow cytometry.

In accordance with the twenty-fifth embodiment, the cleansed biological sample may reflect various degrees of removal of viral infection. For example, the biological sample may be 50% free of viral infection, alternatively, 60% free of viral infection, alternatively, 70% free of viral infection, alternatively, 80% free of viral infection, alternatively, 85% free of viral infection, alternatively, 90% free of viral infection, alternatively, 95% free of viral infection, alternatively, 99% free of viral infection, or alternatively, 100% free of viral infection.

According to a twenty-fifth embodiment of the invention, there is provided a cleansed biological sample prepared in accordance with the method of the twenty-fourth embodiment of the invention.

According to a twenty-sixth embodiment of the invention, there is provided a method of diagnosis of infection of a subject by a virus of the herpesvirideae group, the method comprising:
  (a) contacting a biological sample of the subject with the ligand of the sixth embodiment,
  (d) detecting the presence of the ligand or fragment thereof selectively bound to the polypeptide of the second embodiment.

According to a twenty-seventh embodiment of the invention, there is provided a method of diagnosis of infection of a subject by a virus of the herpesvirideae group, the method comprising:
  (d) obtaining a biological sample from said subject;
  (e) contacting said biological sample with the nucleic acid sequence of the first embodiment; and
  (f) detecting the presence or absence of hybridisation between the nucleic acid sample of said biological sample and the nucleic acid sequence of the first embodiment.

In the method of the twenty-seventh embodiment, the nucleic acid sequence of the first embodiment or a fragment thereof typically corresponds to a region of the nucleic acid sequence which is capable of selectively hybridising to the nucleic acid encoding the IL-10 homologue expressed during the latent phase of infection by a virus of the herpesvirideae group. The region of the nucleic acid sequence of the first embodiment may correspond to a nucleic acid region which encodes polypeptides/peptides of the C-terminal end of the IL-10 homologue. This region may take the form of primers/oligos for a PCR reaction or a oligonucleotide as a hybridisation probe. For instance, the oligonucleotides used in this process may correspond to those set out in any one of SEQ ID NOS:2-9. Moreover, the oligonucleotide may correspond to the sequence set forth in SEQ ID NO:9.

The hybridisation may occur and be detected through techniques that are standard and routine amongst those skilled in the art, and include southern and northern hybridisation, polymerase chain reaction (PCR) and ligase chain reaction (LCR).

In relation to any one of the tenth through to twenty-seventh embodiments of the invention, the disease state may be one arising from infection by a virus of the herpesvirideae group. More typically, the disease is selected from the group consisting of: Epstein-Barr virus, human herpesvirus (HHV)-6, HHV-7, HHV-8, varicella zoster virus, herpes simplex type 1 and type 2 and cytomegalovirus. The biological sample referred to in any one of the seventeenth, eighteenth or twenty-seventh embodiment of the invention may correspond to a nucleic acid sample, which itself may be a DNA or RNA sample.

DEFINITIONS

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides.

As used herein the term "polypeptide" means a polymer made up of amino acids linked together by peptide bonds.

The term "purified" means that the material in question has been removed from its host, and associated impurities reduced or eliminated. Essentially, it means an object species is the predominant species present (ie., on a molar basis it is more abundant than any other individual species in the composition), and preferably a substantially purified fraction is a composition wherein the object species comprises at least about 30 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The term "fragment" refers to a nucleic acid or polypeptide molecule that encodes a constituent or is a constituent of the full-length human IL-10 homologue or variant thereof, wherein said IL-10 homologue is expressed during the latent phase of infection by a virus of the herpesvirideae group. In terms of the polypeptide the fragment possesses qualitative biological activity in common with the homologue of human IL-10. However, fragments of a nucleic acid sequence, do not necessarily need to encode polypeptides which retain biological activity, for example, hybridisation probes or PCR primers. The fragment may be derived from the full-length homologue of human IL-10 or alternatively may be synthesised by some other means, for example chemical synthesis.

The term "variant" as used herein refers to substantially similar sequences. Generally, nucleic acid sequence variants of the invention encode a polypeptide which possesses qualitative biological activity in common with the homologue of human IL-10. Generally, polypeptide sequence variants of the invention also possess qualitative biological activity in common with the homologue of human IL-10. Further, these polypeptide sequence variants may have at least 25%, 30%, 35%, 40%, 45%, 50%, 55%, 60%, 65%, 70%, 75%, 80%, 85%, 90%, 95%, 96%, 97%, 98% or 99% sequence identity to the human IL10 receptor.

As used herein "sequence identity" refers to the residues in two sequences that are the same when aligned for maximum correspondence over a specified window of comparison by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), *Journal of Molecular Biology*, 48, 443-453).

Further, a variant polypeptide may include analogues, wherein the term "analogue" as used herein with reference to a polypeptide means a polypeptide which is a derivative of the polypeptide of the invention, which derivative comprises addition, deletion, substitution of one or more amino acids, such that the polypeptide retains substantially the same function as the human IL-10 homologue expressed during the latent phase of infection by a virus of the herpesvirideae group identified above.

The term "conservative amino acid substitution" as used herein refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

The term "antibody" means an immunoglobulin molecule able to bind to a specific epitope on an antigen. Antibodies can be comprised of a polyclonal mixture, or may be monoclonal in nature. Further, antibodies can be entire immunoglobulins derived from natural sources, or from recombinant sources. The antibodies of the present invention may exist in a variety of forms, including for example as a whole antibody, or as an antibody fragment, or other immunologically active fragment thereof, such as complementarity determining regions. Similarly, the antibody may exist as an antibody fragment having functional antigen-binding domains, that is, heavy and light chain variable domains. Also, the antibody fragment may exist in a form selected from the group consisting of, but not limited to: Fv, $F_{ab}$, $F(ab)_2$, scFv (single chain Fv), dAb (single domain antibody), bi-specific antibodies, diabodies and triabodies.

As used herein the term "treatment", refers to any and all uses which remedy a disease state or symptoms, prevent the establishment of disease, or otherwise prevent, hinder, retard, or reverse the progression of disease or other undesirable symptoms in any way whatsoever.

As used herein, the term "selectively binds" refers to the ability of antibodies to the homologue of human IL-10 expressed during the latent phase of infection by a virus of the herpesvirideae group to preferentially bind to specified proteins and mimetopes thereof of the present invention. Binding can be measured using a variety of methods standard in the art including enzyme immunoassays (e.g., ELISA), immunoblot assays, etc. An anti-IL-10 homologue antibody selectively binds to the IL-10 homologue in such a way as to reduce the activity of that protein.

As used herein, the term "selectively hybridises" refers to the ability of nucleic acids, such as probes or primers, of the present invention to preferentially bind to nucleic acids encoding a human IL-10 homologue expressed during the latent phase of infection by a virus of the herpesvirideae group. In indicating that a sequence "selectively hybridises", the term includes reference to hybridisation, under stringent hybridisation conditions, to a specific nucleic acid target sequence to a detectably greater degree than a non-target nucleic acid sequence.

As used herein the term "therapeutically effective amount" includes within its meaning a non-toxic but sufficient amount of an agent or compound to provide the desired therapeutic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

In the context of this specification, the term "comprising" means "including principally, but not necessarily solely".

Furthermore, variations of the word "comprising", such as "comprise" and "comprises", have correspondingly varied meanings.

BRIEF DESCRIPTION OF THE DRAWINGS

Preferred embodiments of the present invention will now be described, by way of example only, with reference to the accompanying drawings.

(A) Schematic representation of the CMV genome with the UL111.5A transcript expanded to show the position of primers (arrow heads) and probe (open box) used in this study. (B) RT-PCR analysis of UL111.5A-region gene expression in latently infected GM-Ps. Detection of UL111.5A region transcripts in CMV strain Toledo productively infected HFFs (day 4 p.i) and latently infected GM-Ps (day 14 p.i) (B) and CMV strain Towne (C) and AD169 (D) latently infected GM-Ps (day 14 p.i). Panels B-D show ethidium bromide-stained agarose gels (upper panel) and the corresponding Southern blots (lower panel) of products generated from RT-PCR analysis for UL111.5A region transcripts. The size of the RT-PCR products are indicated with arrows and the numbers to the left of the gels indicate the size of the adjacent molecular weight size markers (M). Presence (+) or absence (−) of the reverse transcriptase (RT) in the reaction mixture are indicated.

Figure 2:
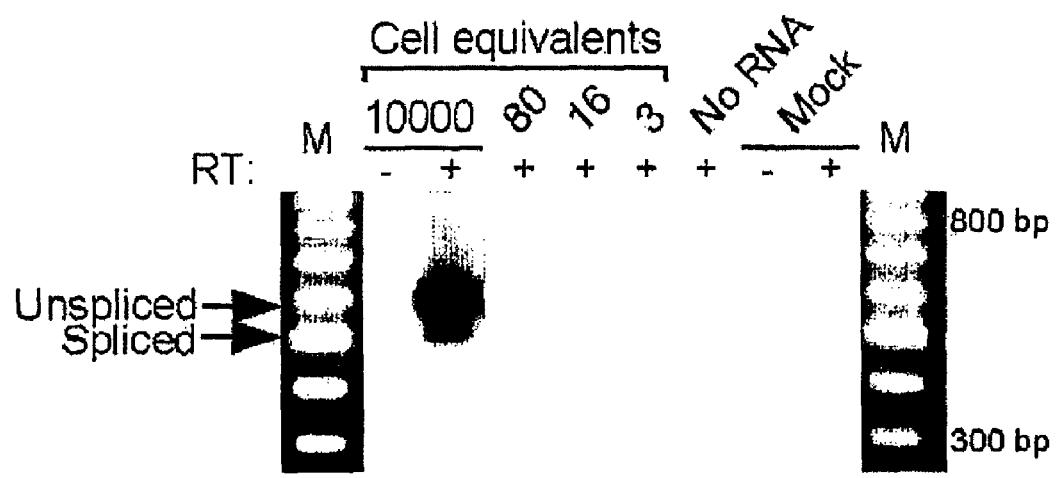

FIG. 2. Enumeration of GM-Ps expressing UL111.5A-region transcripts.

Southern blot of RT-PCR products showing detection of UL111.5A-region transcripts. Latently infected GM-Ps were counted and serially diluted to give an average of 10000, 80, 16, and 3 cells per reaction as indicated above lanes. Arrows adjacent to the lanes indicate the position of predicted spliced and unspliced RT-PCR products amplified using primers JAS-F1 and JAS-R5. Cells from a mock-infected GM-P culture (Mock) and a sample without RNA (No RNA) were included as negative controls. The presence (+) or absence (−) of reverse transcriptase (RT) in each reaction is indicated. Ethidium bromide stained 100 bp DNA ladder (M) is shown on both sides of the panel.

Figure 3:
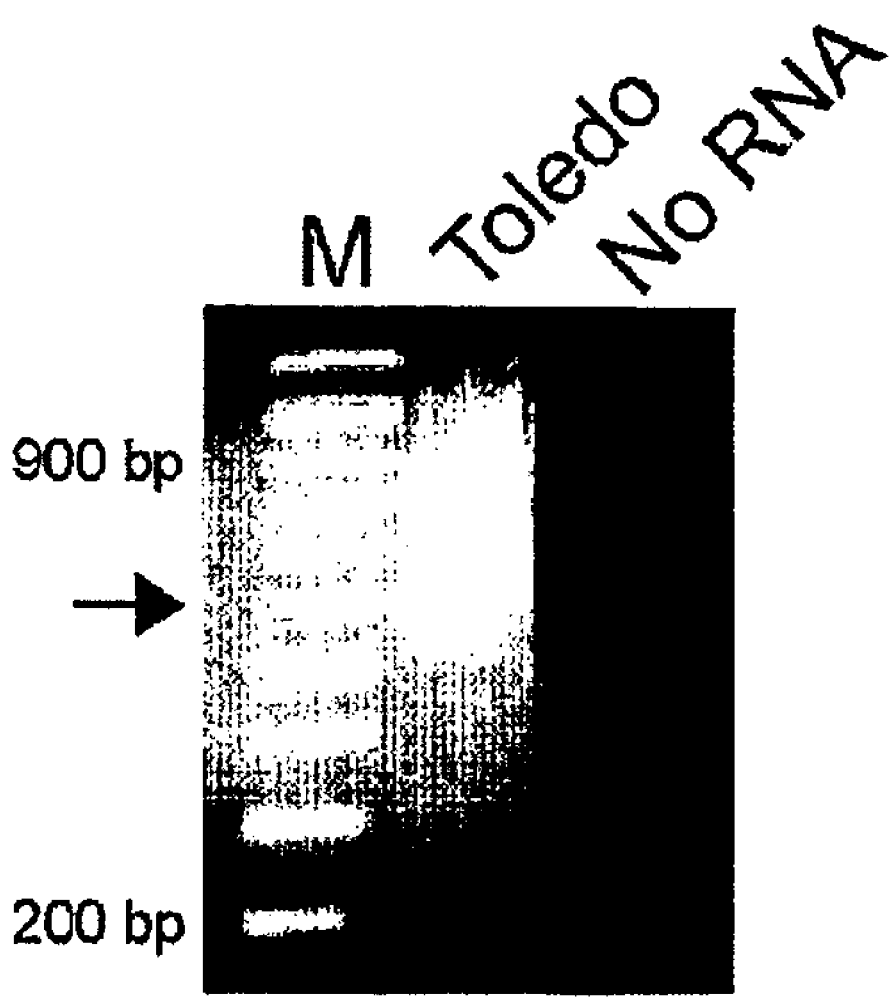

FIG. 3. Determination of 3' terminus of UL111.5A-region transcripts expressed during latent CMV infection of GM-Ps.

Ethidium bromide-stained agarose gel of 3' RACE PCR products derived from RNA extracted from GM-Ps latently infected with CMV strain Toledo. The arrow indicates a single 3' RACE PCR product of approximately 600 bp following nested amplification using primer JAS-F1 and UPM for the $1^{st}$ round and JAS-P3 and NUP for the $2^{nd}$ round. A negative control containing no RNA template and a 100 bp DNA ladder (M) are indicated.

Figure 4:
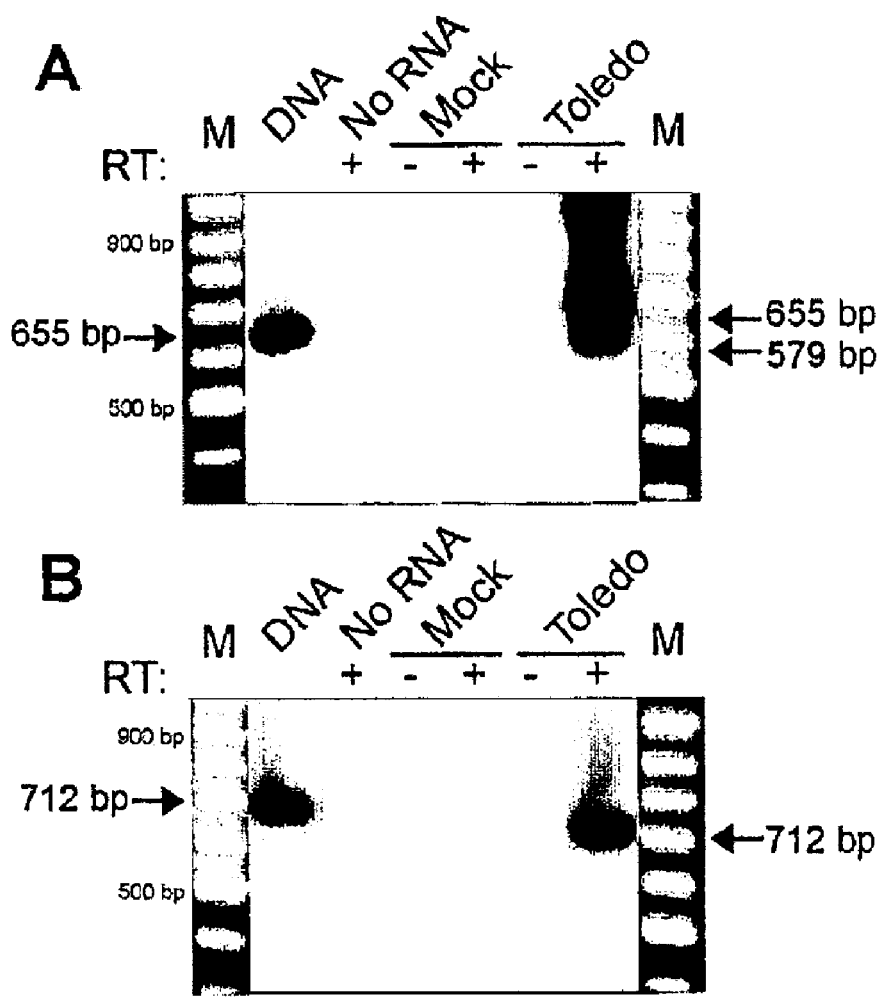

FIG. 4. Determination of the 5' terminus of UL111.5A-region transcripts expressed during latent CMV infection of GM-Ps.

Southern blots of RT-PCR products derived from RNA extracted from mock or CMV strain Toledo infected GM-Ps. (A) RT-PCR products amplified using the forward primer JAS-52. Arrows indicate the position of 579 bp spliced and 655 bp unspliced products. (B) RT-PCR products amplified using the forward primer JAS-53. Arrows indicate the position of the predicted 712 bp unspliced product, but no spliced product was detected. DNA extracted from productively infected HFFs was included as a positive control for the PCR reactions. A negative control containing no RNA template and a 100 bp DNA ladder (M) are indicated. The presence (+) or absence(−) of reverse transcriptase (RT) in each reaction mixture is indicated.

Figure 5:
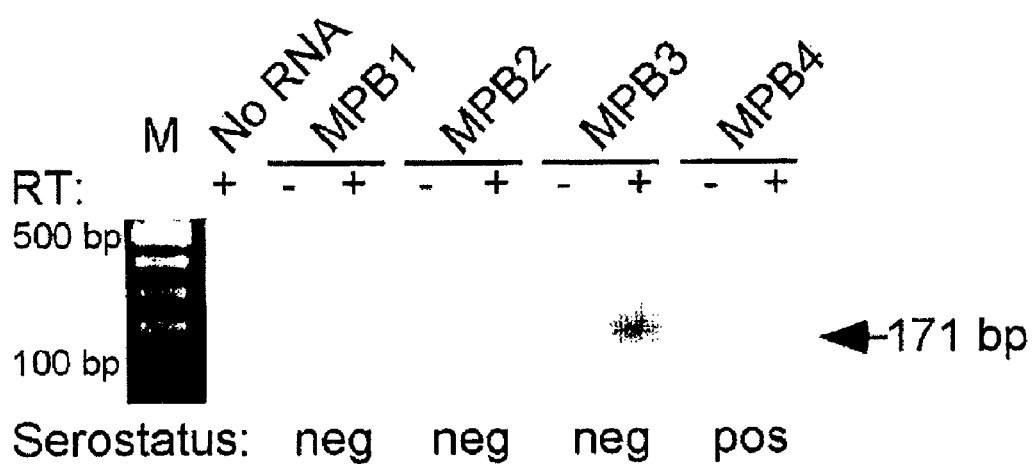

FIG. 5. Spliced UL111.5A-region transcripts are expressed during natural latent infection Southern blot of mobilized peripheral blood samples (MPB1-MPB4) after hemi-nested PCR amplification using primers JAS-F1 and JAS-B1 ($1^{st}$ round) and JAS-F1 and JAS-R1 ($2^{nd}$ round). The arrow indicates the position of a predicted 171 bp spliced UL111.5A-region transcript product. A negative control containing no RNA template and a 100 bp DNA ladder (M) are indicated. The presence (+) or absence(−) of reverse transcriptase (RT) in each reaction mixture is indicated.

Figure 6:
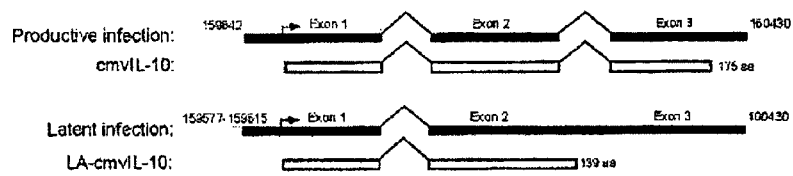

FIG. 6. (A) Summary of the structure of UL111.5A-region transcripts expressed during productive and latent infection.

Upper lines show the double spliced UL111.5A transcript expressed during productive infection and the corresponding 175 amino acid open reading frame (ORF) that encodes cmvIL-10 (productive phase expression product). Lower lines show the single spliced UL111.5A-region transcript expressed during latent infection and its corresponding ORF that encodes a putative 139 amino acid protein termed LA-cmvIL-10, and referred to as human IL-10 homologue. Black boxes and open boxes depict transcripts and ORFs, respectively. Nucleotide position numbers (AD169 genome) of the start and stop sites of transcription are indicated and the region encompassing the start site of the spliced transcript expressed during latency is shown as a grey box. The first methionine residue is indicated by a right angled arrow.

(B) Alignment of the amino acid sequences of human IL-10 and LA-cmvIL-10.

Identical amino acids are shown in white letters on a black background and conserved amino acids are shown as + signs. Amino acid residues are numbered from the first methionine. The amino acid sequence of the IL-10 homologue expressed by CMV during productive infection (cmvIL-10) is also shown.

Figure 7:
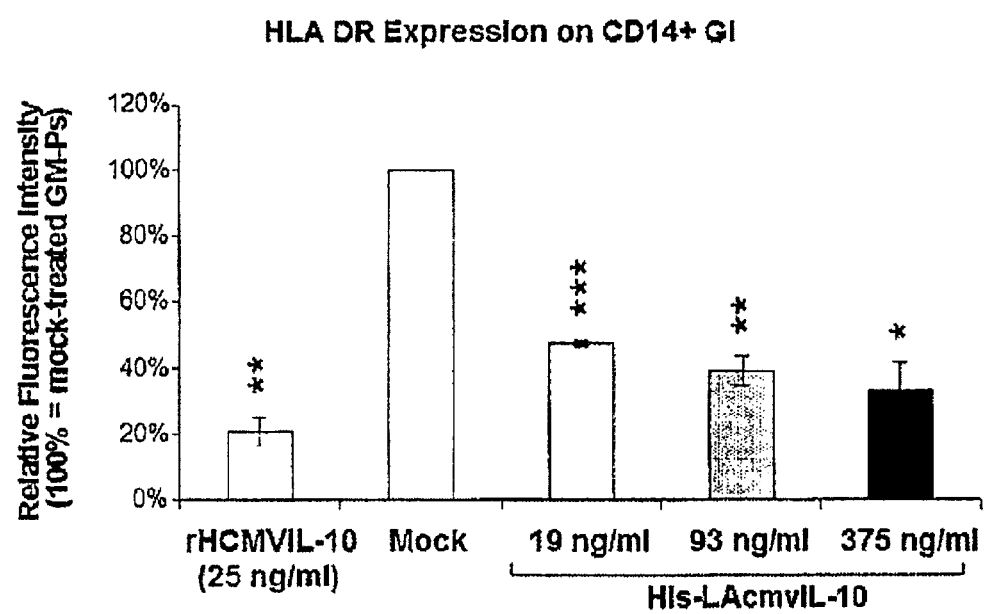

FIG. 7. Flow cytometry-based analysis of MHC class II (HLA-DR) expression on the surface of granulocyte macrophage progenitor cells (GM-Ps) following treatment with recombinant LAcmv-IL10 protein generated from a transcript expressed from the UL111.5A region during latent HCMV The relative fluorescence intensity (RFI) of surface HLA-DR molecules on CD14+ primary human GM-Ps incubated for 48 hours with varying concentrations of recombinant His-tagged LAcmvIL-10 (His-LAcmvIL-10) or commercially available recombinant HCMVIL-10 (positive control) are shown with the means and standard errors calculated from 3 independent replicate experiments. Significant differences to the Mock-treated control were determined using 1-tailed, paired Student's t test and are indicated as follows: *P<0.05, P<0.005, *P<0.0005. These results show that LAcmvIL10 functions to downregulate cell-surface MHC class II (HLA-DR) on primary human GM-Ps. This effect on HLA-DR was dose-dependent.

DETAILED DESCRIPTION OF THE INVENTION

In isolating the nucleic acid of the invention, RNA was extracted from cells, such as myeloid progenitor cells-GM-Ps, or human foreskin fibroblasts-HFFs and subjected to reverse transcription-PCR based techniques to amplify the nucleic acid sequence of the transcript that encodes the cytomegalovirus (CMV) IL-10-homologue. In doing so, random primers were used to prime the reverse transcription reaction, and CMV-specific primers to amplify regions encoding cmvIL10.

The amplified region was then cloned and the nucleic acid sequence determined by standard sequencing techniques. The resulting nucleic acid sequence was then used as a template to derive the amino acid sequence (ie polypeptide sequence). The homology of this latent CMV-encoded polypeptide to human IL-10 was determined by searching against a database of known polypeptide sequences using a computer-based amino acid alignment program.

Nucleic Acid Sequence

Typically, the nucleic acid molecule of the first embodiment also includes within its scope a variant or fragment of the nucleic acid sequence, wherein said variant or fragment encodes a polypeptide having a biological activity which is functionally the same as the polypeptide (or fragment thereof) encoded by the nucleic acid molecule of the invention, in particular the nucleic acid sequence defined in SEQ ID NO:1 wherein said variant can be located and isolated using standard techniques in molecular biology, without undue trial and experimentation.

The degree of homology between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), *Journal of Molecular Biology,* 48, 443-453). Using GAP with the following settings for DNA sequence comparison: GAP creation penalty of 5.0 and GAP extension penalty of 0.3.

Nucleic acid molecules may be aligned to each other using the Pileup alignment software, available as part of the GCG program package, using, for instance, the default settings of gap creation penalty of 5 and gap width penalty of 0.3.

The nucleic acid molecule may also include within its scope a variant capable of hybridising to the nucleic acid molecules of the invention, in particular the nucleic acid sequences defined in SEQ ID NOS:1-9 under conditions of low stringency, more preferably, medium stringency and still more preferably, high stringency. Low stringency hybridisation conditions may correspond to hybridisation performed at 50° C. in 2×SSC.

Suitable experimental conditions for determining whether a given nucleic acid molecule hybridises to a specified nucleic acid may involve presoaking of a filter containing a relevant sample of the nucleic acid to be examined in 5×SSC for 10 min, and prehybridisation of the filter in a solution of 5×SSC, 5×Denhardt's solution, 0.5% SDS and 100 μg/ml of denatured sonicated salmon sperm DNA, followed by hybridisation in the same solution containing a concentration of 10 ng/ml of a $^{32}$P-dCTP-labeled probe for 12 hours at approximately 45° C., in accordance with the hybridisation methods as described in Sambrook et al. (1989; Molecular Cloning, A Laboratory Manual, 2nd edition, Cold Spring Harbour, N.Y.).

The filter is then washed twice for 30 minutes in 2×SSC, 0.5% SDS at least 55° C. (low stringency), at least 60° C. (medium stringency), at least 65° C. (medium/high stringency), at least 70° C. (high stringency), or at least 75° C. (very high stringency). Hybridisation may be detected by exposure of the filter to an x-ray film.

Further, there are numerous conditions and factors, well known to those skilled in the art, which may be employed to alter the stringency of hybridisation. For instance, the length and nature (DNA, RNA, base composition) of the nucleic acid to be hybridised to a specified nucleic acid; concentration of salts and other components, such as the presence or absence of formamide, dextran sulfate, polyethylene glycol etc; and altering the temperature of the hybridisation and/or washing steps.

Further, it is also possible to theoretically predict whether or not two given nucleic acid sequences will hybridise under certain specified conditions. Accordingly, as an alternative to the empirical method described above, the determination as to whether a variant nucleic acid sequence will hybridise to the nucleic acid molecule defined in accordance with the first embodiment, or more specifically, the nucleic acid of SEQ ID NO:1, can be based on a theoretical calculation of the $T_m$ (melting temperature at which two heterologous nucleic acid sequences with known sequences will hybridise under specified conditions, such as salt concentration and temperature.

In determining the melting temperature for heterologous nucleic acid sequences ($T_{m(hetero)}$) it is necessary first to determine the melting temperature ($T_{m(homo)}$) for homologous nucleic acid sequence. The melting temperature ($T_{m(homo)}$) between two fully complementary nucleic acid strands (homoduplex formation) may be determined in accordance with the following formula, as outlined in Current Protocols in Molecular Biology, John Wiley and Sons, 1995, as:

$$T_{m(homo)}=81.5°\ C.+16.6(\log M)+0.41(\%\ GC)-0.61(\%\ \text{form})-500/L$$

M=denotes the molarity of monovalent cations,

% GC=% guanine (G) and cytosine (C) of total number of bases in the sequence,

% form=% formamide in the hybridisation buffer, and

L=the length of the nucleic acid sequence.

$T_m$ determined by the above formula is the $T_m$ of a homoduplex formation ($T_{m(homo)}$) between two fully complementary nucleic acid sequences. In order to adapt the $T_m$ value to that of two heterologous nucleic acid sequences, it is assumed that a 1% difference in nucleotide sequence between two heterologous sequences equals a 1° C. decrease in $T_m$. Therefore, the $T_{m(hetero)}$ for the heteroduplex formation is obtained through subtracting the homology % difference between the analogous sequence in question and the nucleotide probe described above from the $T_{m(homo)}$.

Typically the nucleic acid molecule defined in SEQ ID NO:1 also includes within its scope a nucleic acid molecule which is an oligonucleotide fragment thereof. Typically, the oligonucleotide fragment is between about 15 to about 725 nucleotides in length. More typically, the oligonucleotide fragment is between about 15 to about 600 nucleotides in length. Even more typically, the oligonucleotide fragment is between about 15 to about 150 nucleotides in length. Even more typically still, the oligonucleotide fragment is between about 15 to about 90 nucleotides in length. Yet still more typically, the oligonucleotide fragment is between about 15 to about 75 nucleotides in length.

Furthermore, the oligonucleotide fragments may encode polypeptides or peptides thereof derived from the C-terminal end of the IL-10 homologue. Examples of such oligonucleotides are set out herein as SEQ ID NOS: 2 -9.

Polypeptide

Typically, the polypeptide of the second embodiment also includes within its scope a variant or fragment thereof, wherein said variant or fragment has biological activity which is functionally the same as the polypeptide defined in SEQ ID NO:10.

The human IL-10 homologue of the invention generally shares about 20 to 30% amino acid sequence identity to human IL-10, and more specifically, about 27% amino acid sequence identity to human IL-10. In addition, when considered across their total lengths, the IL-10 homologue shares 72% identity with the cmvIL10, an identity that increases to 91% in a comparison across the first 139 amino acids.

In vitro detection of the polypeptides or variants or fragments thereof of the present invention may be achieved using a variety of techniques including ELISA (enzyme linked immunosorbent assay), Western blotting, immunoprecipitation and immunofluorescence. Such techniques are commonly used by those of skill in the art. Similarly, suitable techniques of the in vivo detection of the polypeptide, or fragments or analogues thereof, including immunohistochemistry using a labelled anti-human IL-10 homologue expressed during the latent phase of infection by a virus of the herpesvirideae group, such as an IL-10 homologue expressed during the latent phase of infection by cytomegalovirus, will be readily understood by persons skilled in the art.

In accordance with the present invention, fusion proteins may also be engineered to improve characteristics of the IL-10 homologue or variant or fragment thereof. For example, a region of additional amino acids, particularly charged amino acids, may be added to the N-terminus of the IL-10 homologue to improve stability during purification from a host cell. Alternatively, peptide moieties may be added to the polypeptide to facilitate purification. Such regions may be removed prior to final preparation of the polypeptide. The addition of peptide moieties to facilitate handling of polypeptides are routine techniques well known to those of skill in the art.

Typically the polypeptide defined in accordance with the second embodiment wherein such a polypeptide includes within its scope that set out in SEQ ID NO:10, also includes within its scope a peptide fragment thereof. The peptide fragment may be between about 5 to about 150 amino acids in length. Alternatively, the peptide fragment may be between about 8 to about 100 amino acids in length. Alternatively, the peptide fragment may be between about 8 to about 50 amino acids in length. Alternatively, the peptide fragment may be between about 8 to about 35 amino acids in length. Alternatively, the peptide fragment may be between about 8 to about 25 amino acids in length. Alternatively, the peptide fragment may be between about 8 to about 15 amino acids in length. Alternatively, the peptide fragment may be between about 8 to about 12 amino acids in length. Alternatively, the peptide fragment is about 12 amino acids in length.

Furthermore, the peptide fragment may be derived from the C-terminal end of the IL-10 homologue. For example, the fragment may comprise one or more amino to acids, or a combination thereof, of a unique 12 amino acid sequence VSVSVAALSAQR (SEQ ID NO: 11), and in such an example, the peptides may overlap this unique region.

Uses of the Interleukin 10 (IL-10) Homologue

Antibodies

In preparing antibodies for use in the invention, a protocol such as that set out in the following may be used. The cDNA sequence of the IL-10 homologue or variant or fragment thereof is cloned into a vector, such as pcDNA3.1 myc-His to generate a carboxyl terminal myc-His tagged IL-10 homologue or expression vector. This vector is then transformed into *E. coli* and the expressed protein affinity purified. The purified IL-10 homologue protein may be used to generate rabbit polyclonal antiserum using methods known in the art, such as, a commercial production service. In addition to whole IL-10 homologue or variant or fragment thereof protein, unique synthetic peptides, such as peptides whose amino acid sequence overlaps all or part of the unique, non homologous C-terminal portion of IL-10 homologue or variant or fragment thereof as (VSVSVAALSAQR) (SEQ ID NO: 11) may be used as immunogens to generate rabbit polyclonal antiserum. The specificity of the resulting antibodies will be determined by immunoblotting against purified IL-10 homologue, human IL10 and cmvIL10 (human IL10 and cmvIL10 are available commercially). Based upon these results, monoclonal antibodies can be generated against whole or a part of the IL-10 homologue.

The present invention provides antibodies or fragments thereof that selectively bind to the human IL-10 homologue of the present invention, as well as variants or fragments thereof. Suitable antibodies include, but are not limited to polyclonal, monoclonal, chimeric, humanised, single chain, Fab fragments, and an Fab expression library. Antibodies of the present invention may act as agonists or antagonists of the IL-10 homologue, or fragments or analogues thereof.

Preferably antibodies are prepared from discrete regions or fragments of the IL-10 homologue, in particular those involved in conferring protease activity and/or partner or substrate binding. An antigenic IL-10 homologue contains at least about 5, and preferably at least about 9, amino acids.

Methods for the generation of suitable antibodies will be readily appreciated by those skilled in the art. For example, an anti-IL-10 homologue monoclonal antibody, typically containing Fab portions, may be prepared using the hybridoma technology described in Antibodies-A Laboratory Manual, Harlow and Lane, eds., Cold Spring Harbor Laboratory, N.Y. (1988).

In essence, in the preparation of monoclonal antibodies directed toward latent phase polypeptides, such as cytomegalovirus herpesvirideae fragment or variants thereof, any technique that provides for the production of antibody molecules by continuous cell lines in culture may be used. These include the hybridoma technique originally developed by Kohler et al., Nature, 256:495-497 (1975), as well as the trioma technique, the human B-cell hybridoma technique [Kozbor et al., Immunology Today, 4:72 (1983)], and the EBV-hybridoma technique to produce human monoclonal antibodies [Cole et al., in Monoclonal Antibodies and Cancer Therapy, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980).

In summary, a means of producing a hybridoma from which the monoclonal antibody is produced, a myeloma or other self-perpetuating cell line is fused with lymphocytes obtained from the spleen of a mammal hyperimmunised with a recognition factor-binding portion thereof, or recognition factor, or an origin-specific DNA-binding portion thereof. Hybridomas producing a monoclonal antibody useful in practicing this invention are identified by their ability to immunoreact with the present recognition factor and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Similarly, there are various procedures known in the art which may be used for the production of polyclonal antibodies to the IL-10 homologue, or fragments, or variants thereof.

For the production of a IL-10 homologue polyclonal antibody, various host animals can be immunized by injection with the IL-10 homologue, or a fragment or variant thereof, including but not limited to rabbits, mice, rats, sheep, goats, etc. Further, the IL-10 homologue or fragment or variant thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

Screening for the desired IL-10 homologue antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary anti latent phase cytomegalovirus polypeptide antibody. Alternatively, the anti-IL-10 homologue antibody may be detected by virtue of its binding with a secondary antibody or reagent which is appropriately labelled. A variety of methods are known in the art for detecting binding in an immunoassay and are within the scope of the present invention.

Antibodies of the present invention can be used in diagnostic methods and kits that are well known to those of ordinary skill in the art to detect qualitatively or quantify latent phase cytomegalovirus in a body fluid or tissue, and results from these tests can be used to diagnose or determine predisposition to a diseases arising from infection in a subject by a virus of the herpesvirideae group.

The antibody or fragment thereof raised against the IL-10 homologue or a fragment or analogue thereof has binding affinity for the polypeptide. Preferably, the antibody or fragment thereof has binding affinity or avidity greater than about $10^5$ $M^{-1}$, more preferably greater than about $10^6$ $M^{-1}$, more preferably still greater than about $10^7$ $M^{-1}$ and most preferably greater than about $10^8$ $M^{-1}$.

In terms of obtaining a suitable amount of an antibody according to the present invention, one may manufacture the antibody(s) using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography may be used to remove residual proteins, solvents/detergents and nucleic acids. The purified antibody may be further purified and formulated into 0.9% saline using gel filtration columns. The formulated bulk preparation may then be sterilised and viral filtered and dispensed.

In a related aspect, the invention may feature a monoclonal antibody, or an Fab, $(Fab)_2$, scFv (single chain Fv), dAb (single domain antibody), bi-specific antibodies, diabodies and triabodies, or other immunologically active fragment thereof (eg., a CDR-region). Such fragments are useful as immunosuppressive agents. Alternatively, the antibody of the invention may have attached to it an effector or reporter molecule. For instance, an antibody or fragment thereof of the invention may have a macrocycle, for chelating a heavy metal atom, or a toxin, such as ricin, attached to it by a covalent bridging structure. In addition, the Fc fragment or $CH_3$ domain of a complete antibody molecule may be replaced or conjugated by an enzyme or toxin molecule, such as chelates, toxins, drugs or prodrugs, and a part of the immunoglobulin chain may be bonded with a polypeptide effector or reporter molecule, such as biotin, fluorochromes, phosphatases and peroxidases. Bispecific antibodies may also be produced in accordance with standard procedures well known to those skilled in the art.

The present invention further contemplates genetically modifying the antibody variable and/or constant regions to include effectively homologous variable and constant region amino acid sequences. Generally, changes in the variable region will be made to improve or otherwise modify antigen binding properties of the antibody or fragment thereof. Changes in the constant region will, in general, be made in order to improve or otherwise modify biological properties, such as complement fixation, interaction with membranes, and other effector functions.

In the present context, effectively homologous refers to the concept that differences in the primary structure of the variable region of the antibody or fragment thereof may not alter the binding characteristics of the antibody or fragment thereof. Changes of amino acids are permissable in effectively homologous sequences so long as the resultant antibody or fragment thereof retains its desired property.

Amino acid changes in the polypeptide or the antibody or fragment thereof may be effected by techniques well known to persons skilled in the relevant art. For example, amino acid changes may be effected by nucleotide replacement techniques which include the addition, deletion or substitution of nucleotides, under the proviso that the proper reading frame is maintained. Exemplary techniques include random mutagenesis, site-directed mutagenesis, oligonucleotide-mediated or polynucleotide-mediated mutagenesis, deletion of selected region(s) through the use of existing or engineered restriction enzyme sites, and the polymerase chain reaction.

Modulator and Inhibitor Compounds

In addition to specific anti-IL-10 homologue antibodies, the polypeptides of the present invention, and fragments or variants thereof are particularly useful for the screening and identification of compounds and agents that interact with the IL-10 homologue. In particular, desirable compounds include those that modulate the activity of the latent phase of a virus of the herpesvirideae group. Such compounds may modulate by activating, increasing, inhibiting or preventing latent phase activity. Suitable compounds may exert their effect during the latent phase of a virus of the herpesvirideae group by virtue of either a direct (for example binding) or indirect interaction.

Compounds which bind, or otherwise interact with the IL-10 homologue, and specifically compounds which modulate the activity of the IL-10 homologue, may be identified by a variety of suitable methods. Interaction and/or binding may be determined using standard competitive binding assays or two-hybrid assay systems.

For example, the two-hybrid assay is a yeast-based genetic assay system (Fields and Song, 1989) typically used for detecting protein-protein interactions. Briefly, this assay takes advantage of the multi-domain nature of transcriptional activators. For example, the DNA-binding domain of a known transcriptional activator may be fused to the IL-10 homologue, or fragment or variant thereof, and the activation domain of the transcriptional activator fused to a candidate protein. Interaction between the candidate protein and the IL-10 homologue, or fragment or variant thereof, will bring the DNA-binding and activation domains of the transcriptional activator into close proximity. Interaction can thus be detected by virtue of transcription of a specific reporter gene activated by the transcriptional activator.

Alternatively, affinity chromatography may be used to identify human IL-10 homologue binding partners. For example, an IL-10 homologue or fragment or variant thereof, may be immobilised on a support (such as sepharose) and cell lysates passed over the column. Proteins binding to the immobilised IL-10 homologue, fragment or analogue can then be eluted from the column and identified. Initially such proteins may be identified by N-terminal amino acid sequencing for example.

Alternatively, in a modification of the above technique, a fusion protein may be generated by fusing the IL-10 homologue, fragment or variant to a detectable tag, such as alkaline phosphatase, and using a modified form of immunoprecipitation as described by Flanagan and Leder (1990).

Methods for detecting compounds that modulate the IL-10 homologue activity may involve combining the IL-10 homologue with a candidate compound and a suitable labelled substrate and monitoring the effect of the compound on the IL-10 homologue by changes in the substrate (may be determined as a function of time). Suitable labelled substrates include those labelled for colourimetric, radiometric, fluorimetric or fluorescent resonance energy transfer (FRET) based methods, for example. Alternatively, compounds that modulate the activity of the IL-10 homologue may be identified by comparing the catalytic activity of IL-10 homologue in the presence of a candidate compound with the catalytic activity of the IL-10 homologue in the absence of the candidate compound.

The present invention also contemplates compounds which may exert their modulatory effect on the IL-10 homologue by altering expression of the protein. In this case, such compounds may be identified by comparing the level of expression of IL-10 homologue in the presence of a candidate compound with the level of expression of IL-10 homologue in the absence of the candidate compound.

IL-10 homologues and appropriate fragments and variants can be used in high-throughput screens to assay candidate compounds for the ability to bind to, or otherwise interact with latent phase viruses of the herpesvirideae group, in particular, latent phase cytomegalovirus. These candidate compounds can be further screened against functional IL-10 homologues to determine the effect on their activity.

It will be appreciated that the above described methods are merely examples of the types of methods which may be employed to identify compounds that are capable of interacting with, or modulating the activity of, the IL-10 homologues, and fragments and analogues thereof, of the present invention. Other suitable methods will be known to persons skilled in the art and are within the scope of the present invention.

By the above methods, compounds can be identified which either activate (agonists) or inhibit (antagonists) activity of latent phase viruses of the herpesvirideae group cytomegalovirus activity. Such compounds may be, for example, antibodies, low molecular weight peptides, nucleic acids or non-proteinaceous organic molecules.

Potential modulators of activity of IL-10 homologues, for screening by the above methods, may be generated by a number of techniques known to those skilled in the art. For example, various forms of combinatorial chemistry may be used to generate putative non-peptide modulators. Additionally, techniques such as nuclear magnetic resonance (NMR) and X ray crystallography, may be used to model the structure of latent phase cytomegalovirus polypeptides, fragments and analogues and computer predictions used to generate possible modulators (in particular inhibitors) that will fit the shape of the substrate binding cleft of the IL-10 homologue.

In addition, IL-10 homologue function may be reduced or inhibited by IL-10 homologue antisense nucleic acids. The therapeutic or prophylactic use of such nucleic acids of at least six nucleotides, generally up to about 150 nucleotides, that are antisense to a gene or cDNA encoding the IL-10 homologue or a portion thereof is also provided herein. In this instance, these IL-10 homologue antisense nucleic acids refer to a nucleic acid capable of hybridising to a portion of an IL-10 homologue RNA (generally mRNA) by virtue of some sequence complementarity, and generally under high stringency conditions. The antisense nucleic acid can be complementary to a coding and/or non-coding region of the IL-10 homologue mRNA. Absolute complementarily to the full IL-10 homologue is not required. Antisense nucleic acids in this form have utility as therapeutics that reduce or inhibit IL-10 homologue function, and can be used in the treatment or prevention of disease states as described herein.

The IL-10 homologue antisense nucleic acids may be of at least six nucleotides and are generally oligonucleotides which range in length from 6 to about 150 nucleotides. For example, the anti-sense oligonucleotide is at least 10 nucleotides, at least 15 nucleotides, at least 100 nucleotides, or at least 125 nucleotides. The oligonucleotides can be DNA or RNA or chimeric mixtures or derivatives or modified versions thereof, single-stranded or double-stranded.

The anti-sense oligonucleotide can be modified at any position on its structure with substituents generally known in the art. The IL-10 homologue antisense oligonucleotide can include at least one modified base moiety which is selected from the group including, but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, 2,2-dimethylguanine, 2-methyl-adenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, pseudouracil, 2-thiocytosine, 5-methyl-2-thiouracil, 2-thiouracil, 4-thiouracil, 5-methyluracil, uracil-5-oxyacetic acid methylester, uracil-5-oxyacetic acid (v), queosine, wybutoxosine, 5-methyl-2-thiouracil, 3-(3-amino-3-N-2-carboxypropyl) uracil, and 2,6-diaminopurine.

In another aspect, the anti-sense oligonucleotide may include at least one modified sugar moiety, such as arabinose, 2-fluoroarabinose, xylulose, and hexose. The oligonucleotide may also include at least one modified phosphate backbone selected from a phosphorothioate, a phosphorodithioate, a phosphoramidothioate, a phosphoramidate, a phosphordiamidate, a methylphosphonate, an alkyl phosphotriester, and a formacetal or analog thereof.

The anti-sense oligonucleotide can be conjugated to another molecule, such as a peptide, hybridisation triggered cross-linking agent, transport agent or a hybridisation-triggered cleavage agent.

Expression of the sequence encoding the IL-10 homologue antisense RNA can be by any promoter known in the art to act in mammalian, including human, cells, and may include inducible or constitutive promoters. Examples of such promoters include: SV40 early promoter region (Bernoist and Chambon, *Nature* 290: 304-310 (1981), promoter in the 3' long terminal repeat of Rous sarcoma virus (Yamamoto et al., *Cell* 22: 787797 (1980), herpes thymidine kinase promoter (Wagner et al., *Proc. Natl. Acad. Sci. U.S.A.* 78: 1441-1445 (1981), or the regulatory sequences of the metallothionein gene (Brinster et al., *Nature* 296: 39-42 (1982), the disclosures of which are incorporated herein by reference.

RNA interference (RNAi) (see, eg. Chuang et al. (2000) *PNAS USA* 97: 4985) can be employed to inhibit the expression of a gene encoding an IL-10 homologue. Interfering RNA (RNAi) fragments, particularly double-stranded RNAi, can be used to generate loss-of IL-10 homologue function. Methods relating to the use of RNAi to silence genes in organisms are known, for instance, Fire et al. (1998) *Nature* 391: 806-811; Hammond, et al. (2001) *Nature Rev, Genet.* 2: 110-1119; Hammond et al. (2000) *Nature* 404: 293-296; Bernstein et al. (2001) *Nature* 409: 363-366; Elbashir et al (2001) *Nature* 411: 494-498; International PCT application No. WO 01/29058; and International PCT application No. WO 99/32619), the disclosures of which are incorporated herein by reference.

Double-stranded RNA expressing constructs are introduced into a host using a replicable vector that remains episomal or integrates into the genome. By selecting appropriate sequences, expression of dsRNA can interfere with accumulation of endogenous mRNA encoding an IL-10 homologue.

Disease Treatment and Diagnosis

Compounds identified by the above methods may be useful as therapeutic agents. These compounds find use, for example, in treating or preventing a disease state in a subject, by administering a therapeutically effective amount of such a compound to the subject. Accordingly, pharmaceutically useful compositions comprising modulators of IL-10 homologue activity for use in treating or preventing disease states associated with IL-10 homologue activity are contemplated. Suitable compositions may be formulated according to known methods such as, for example, by the admixture of a pharmaceutically acceptable carrier and an effective amount of the modulator.

The IL-10 homologue of the present invention and anti-IL-10 homologue antibodies are also particularly useful for determining the presence of a disease state in a subject, or the predisposition of a subject to a disease state, the disease state being one that is associated with infection by a virus of the herpesvirideae group. The IL-10 homologue of the present invention can be used to identify compounds that modulate its activity.

Accordingly, the present invention provides suitable methods for determining the expression of IL-10 homologue transcript in biological samples (including cells and tissues), such as reverse transcription polymerase chain reaction (RT-PCR) and real time quantitative (RTQ) RT-PCR. The invention also provides methods for detecting the expression of IL-10 homologue (as described above).

The polypeptides and methods of the present invention are also particularly useful for diagnosing (presence or predisposition in a subject) diseases or disorders arising from infection by a virus of the herpesvirideae group. In particular, suitable diseases and disorders include those caused by Epstein-Barr virus, human herpesvirus (HHV)-6, HHV-7, HHV-8, varicella zoster virus, herpes simplex type 1 and type 2 and cytomegalovirus.

Modulator and inhibitor compounds and agents of the present invention may be administered as compositions either therapeutically or preventively. In a therapeutic application, compositions are administered to a patient already suffering from a disease, in an amount sufficient to cure or at least partially arrest the disease and its complications. The composition should provide a quantity of the compound or agent sufficient to effectively treat the patient.

The therapeutically effective dose level for any particular patient will depend upon a variety of factors including: the disorder being treated and the severity of the disorder; activity of the compound or agent employed; the composition employed; the age, body weight, general health, sex and diet of the patient; the time of administration; the route of administration; the rate of sequestration of the agent or compound; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

In general, suitable compositions may be prepared according to methods which are known to those of ordinary skill in the art and accordingly may include a pharmaceutically acceptable carrier, diluent and/or adjuvant.

These compositions can be administered by standard routes. In general, the compositions may be administered by the parenteral (e.g., intravenous, intraspinal, subcutaneous or intramuscular), oral or topical route. More preferably administration is by the parenteral route.

The carriers, diluents and adjuvants must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl disteatate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The topical formulations of the present invention, comprise an active ingredient together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, s a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

Kits

In accordance with the present invention, kits containing IL-10 homologue, fragment(s), variant(s) or analogue(s) thereof, or nucleic acids encoding same or fragments thereof, or anti-IL-10 homologue antibodies may be prepared. Such kits may be used, for example, to detect the presence of latent phase infection by a virus of the herpesvirideae group, in particular, cytomegalovirus, in a biological sample. Detection using such kits is useful for a variety of purposes, including but not limited to disease diagnosis, epidemiological studies and performing screening methods of the present invention.

Kits of the present invention comprising one or more anti latent phase herpesviridae antibodies, such as cytomegalovirus antibodies, may further comprise one or more control antibodies which do not react with IL-10 homologues, fragments or variants thereof, of the present invention. Additionally, kits may contain means for detecting the binding of an anti-IL-10 homologue antibody or fragments or analogues thereof, of the present invention For example the one or more anti-IL-10 homologue antibodies may be conjugated to a detectable substrate such as a fluorescent, radioactive or luminescent compound, an enzymatic substrate, or to a second antibody which recognizes the anti-IL-10 homologue antibody and is conjugated to a detectable substrate.

Kits according to the present invention may also include other components required to conduct the methods of the present invention, such as buffers and/or diluents. The kits typically include containers for housing the various components and instructions for using the kit components in the methods of the present invention.

The present invention will now be described with reference to specific examples, which should not be construed as in any way limiting the scope of the invention.

EXAMPLES

Example 1

Cells and Virus Culture

Human fetal liver hematopoietic cells were prepared and cultured as GM-Ps in suspension as described previously (7). On day 4, cells were mock or latently infected with either the sequenced strain AD169 (1), the high passage strain Towne-varRIT$_3$ (6, 15) or the low-passage strain Toledo (16) at a multiplicity of infection (MOI) of 3. GM-Ps were collected and transferred 2-3 times a week for 2 weeks. Human foreskin fibroblasts (HFFs) were used for virus propagation and titer determination by plaque assay.

Samples of bone marrow and mobilized peripheral blood were collected from clinically healthy allograft donors at Westmead Hospital, New South Wales, Australia. Mononuclear cells were isolated on Ficoll gradients and counted prior to RNA extraction.

Example 2

RNA Extraction and RT-PCR Analysis

Total RNA was extracted using a RNAqueous kit (Ambion, Inc). RNA samples (0.2-5 µg) were reverse transcribed in a 20 µl volume in the presence of 1× First Strand Buffer (50 mM Tris-HCl pH 8.3, 75 mM KCl, 3 mM MgCl$_2$), 0.5 mM dNTPs, 20 mM DTT, 40 U RNaseOUT ribonuclease inhibitor, 90 ng of random hexanucleotide primers and 200 U SuperScript II reverse transcriptase (Invitrogen) for 10 min at 25° C. followed by 1.5 hr at 42° C. The reaction was stopped by incubation for 15 min at 70° C.

A 3 µl aliquot of the resulting cDNAs was subjected to PCR amplification in a 50 µl reaction volume containing 50 mM KCl, 20 mM Tris-HCl pH 8.4, 1.5 mM MgCl$_2$, 0.1 mM dNTPs, 0.2 µM forward and reverse primers, 2.5 U Platinum Taq DNA Polymerase (Invitrogen). Briefly, the cycle parameters used in this study were: 94° C. for 45 sec, 60° C. for 1 min, 72° C. for 2 min (cycle A parameters); 94° C. for 30 sec, 68° C. for 30 sec, 72° C. for 2 min (cycle B parameters); 94° C. for 30 sec, 56° C. for 30 sec, 72° C. for 2 min (cycle C parameters). Primer sequences and predicted PCR product sizes are summarised in Table 1 set out below. PCR products were separated by electrophoresis on 1.5% agarose gels and visualised with ethidium bromide. Where indicated, products were Southern blotted and hybridised with a digoxigenin-ddUTP end-labelled oligonucleotide probe (JAS-R6) according to manufacturers protocols (Roche). Probe binding was visualised using the CDP-Star chemiluminescence detection system (Roche).

TABLE 1

Primers and predicted products for PCR analyses

| Primer Sequence | Pair | Unspliced | Spliced intron 1 | Spliced intron 1 & 2 |
|---|---|---|---|---|
| JAS-53 5'-ACTATTCTAACCGCGGAAG-3' (SEQ ID NO: 2) | JAS-R4 | 712 | 636 | 553 |
| | JAS-R5 | 803 | 727 | 644 |

TABLE 1-continued

Primers and predicted products for PCR analyses

| Primer | Sequence | Pair | Unspliced | Spliced intron 1 | Spliced intron 1 & 2 |
|---|---|---|---|---|---|
| JAS-52 | 5'-CATAAAGGACCACCTACCTGGGA-3' (SEQ ID NO: 3) | JAS-R4 | 655 | 579 | 496 |
|  |  | JAS-R5 | 746 | 670 | 587 |
| JAS-F1 | 5'-TACAAAGCCGCAGTGTCGTCCAGAGGATTACG-3' (SEQ ID NO: 4) | JAS-R1 | 247 | 171 | N/A |
|  |  | JAS-B1 | 346 | 270 | N/A |
|  |  | JAS-R5 | 588 | 512 | 429 |
| JAS-P3 | 5'-CAGATTGCAAGATCTCCGCGTCACCTT-3' (SEQ ID NO: 12) | JAS-R4 | 461 | 385 | 302 |
| JAS-R1 | 5'-CAACAACCAGTCCATGACGCTGCATC-3' (SEQ ID NO: 5) | JAS-F1 | 247 | 171 | N/A |
| JAS-B1 | 5'-GTAGATGGATTCTAGCGTCGAGCGCAT-3' (SEQ ID NO: 6) | JAS-F1 | 346 | 270 | N/A |
| JAS-R4 | 5'-TCCTGAGACAGCCGACTAATCACGGAC-3' (SEQ ID NO: 7) | JAS-53 | 712 | 636 | 553 |
|  |  | JAS-52 | 655 | 579 | 496 |
|  |  | JAS-P3 | 461 | 385 | 302 |
| JAS-R5 | 5'-TCTCGAGTGCAGATACTCTTCGAGACGG-3' (SEQ ID NO: 8) | JAS-53 | 803 | 727 | 644 |
|  |  | JAS-52 | 746 | 670 | 587 |
|  |  | JAS-F1 | 588 | 512 | 429 |
| JAS-R6 | 5'-GACCACCGTACCGTCGAGCCACACGGAG-3' (SEQ ID NO: 9) | Probe | N/A | N/A | N/A |

Example 3

3' Rapid Amplification of cDNA Ends (RACE)

The 3' ends of UL111.5A region transcripts were mapped using the SMART™ RACE cDNA Amplification Kit (BD Biosciences). One µg aliquots of DNase treated total RNA from CMV-infected GM-Ps were treated as per manufacturers recommendations. 3' RACE products were generated by amplification of poly dT generated cDNAs for 40 cycles (cycle B parameters) with primers JAS-F1 and UPM (BD Biosciences), followed by a second round of 40 cycles (cycle B parameters) with primers JAS-P3 and NUP (BD Biosciences). 3' RACE products were UA-cloned into the pDrive Cloning Vector (QIAGEN) and plasmid DNA was extracted using the QIAprep Spin Miniprep Kit (QIAGEN).

Example 4

Figure 1:
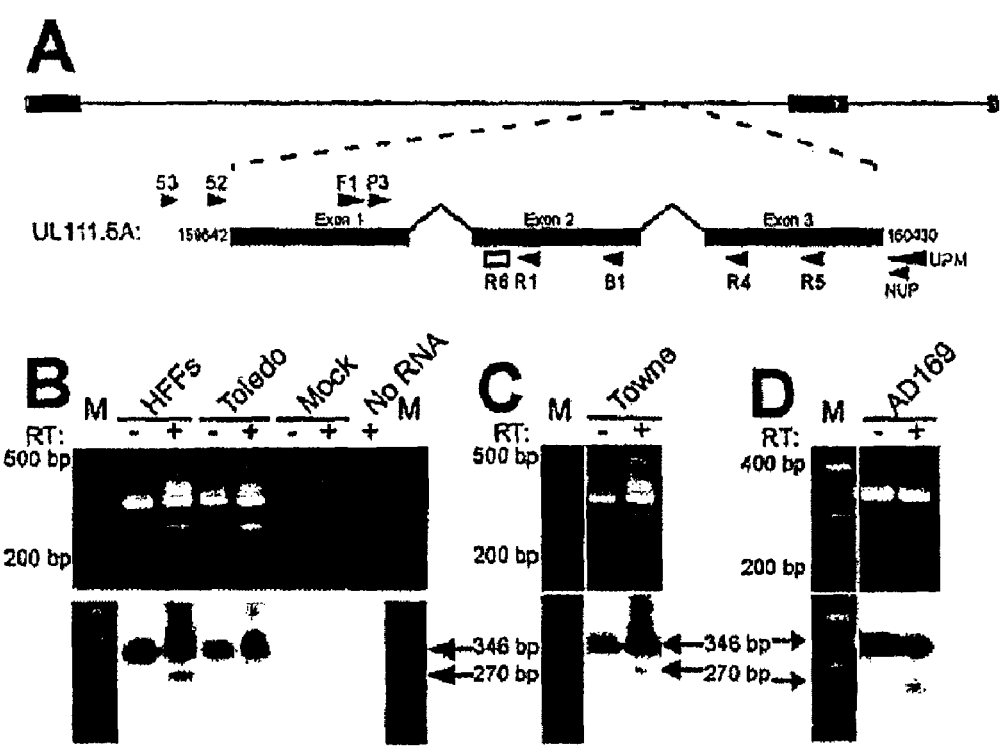
FIG. 1

CMV UL111.5A Region Transcripts are Expressed during Experimental Latent Infection of Granulocyte-Macrophage Progenitors RT-PCR was used to determine whether UL111.5A region transcripts were expressed during experimental latent infection. Human fetal liver-derived GM-Ps were either mock infected or infected with CMV strain Toledo at a MOI=3. On day 14 P.I. total RNA was extracted and reverse transcribed before being amplified for 45 cycles using cycle A parameters with primers JAS-F1 and JAS-B1 which span across UL111.5A intron 1 (FIG. 1A). Amplification of infected GM-P RNA yielded a RT-dependent 270 bp PCR product which was confirmed by Southern blot hybridisation to be UL111.5A specific and which corresponded in size to spliced intron 1 transcripts made in productively infected HFFs (FIG. 1B). A 346 bp genomic sized PCR product was also detected in infected GM-P and HFF samples. Amplification in both the presence and absence of RT indicated that the template for the 346 bp product was either contaminating viral DNA, an unspliced transcript or a combination of the two. Amplification was not detected in mock infected GM-Ps or when RNA was omitted from the reaction mixture.

Assessment of UL111.5A region transcription was extended to GM-P cultures latently infected with either CMV strain AD169 or strain TowneVarRIT$_3$. Like strain Toledo, RT-PCR and Southern blot hybridisation demonstrated that both strain AD169 and strain Towne VarRIT$_3$ expressed spliced UL111.5A region transcripts (FIGS. 1C, D). It was concluded that the UL111.5A region is expressed during experimental latent infection of GM-Ps and that expression is a feature common to multiple strains of CMV.

In the present invention, GM-Ps remained free of infectious virus. Supernatants and cell lysates of $1.5 \times 10^5$ GM-Ps from latently infected cultures were tested for the presence of infectious virus by plaque assay on permissive HFFs. No evidence of plaque formation was detected in either sample (data not shown). Infected GM-P cultures were also assessed by RT-PCR for evidence of productive gene expression. In contrast to RNA from productively infected HFFs, RNA samples from infected GM-P cultures were consistently negative for the expression of UL120, a spliced _65 gene which encodes a putative structural glycoprotein expressed during the productive phase (24 and data not shown).

Example 5

Enumeration of Latently Infected Cells Expressing UL111.5A Region Transcripts The GM-P model of latency used in this study reproducibly results in greater than 90% of cells harbouring viral genomes (19). To determine the proportion of GM-Ps expressing UL111.5A region transcripts, RT-PCR was performed on dilutions of total RNA extracted from GM-Ps 14 days after infection with CMV strain Toledo at a MOI=3. Infected GM-P RNA was treated with DNase to remove contaminating DNA before being diluted such that each reaction contained either 10000, 80, 16 or 3 infected GM-P equivalents. Mock infected GM-P RNA was added to each dilution such that the total amount of RNA per reaction remained constant at 0.5 µg. Random primed cDNA was subjected to 40 cycles of PCR amplification using cycle B parameters with primers JAS-F1 and JAS-R5. A RT-dependent product corresponding to spliced UL 111.5A transcripts was detected at 10000 and 80 infected GM-P equivalents, but became undetectable at 16 infected GM-P equivalents (FIG. 2). In addition, a RT-dependent genomic sized product was also detected at the same dilutions. The DNase treatment of RNA samples and the detection only when RT was included suggests that this product may be an unspliced UL111.5A region transcript. A second round of 30 cycles of PCR using cycle B parameters with primers JAS-P3 and JAS-R4 did not result in detection of either product at a higher dilution (data not shown). Amplification was not detected in mock infected GM-P samples or when RNA was omitted from the reaction mixture (FIG. 2). These data suggest that UL111.5A region transcripts are expressed in between 1/80(1.3%) and 1/16 (6.3%) of experimentally infected GM-Ps.

Example 6

Structural Analysis of UL111.5A Region Transcripts

During productive infection of permissive HFFs, the UL111.5A transcript is comprised of 2 introns and 3 exons whose 5' and 3' ends have previously been defined (10, 12). This transcript codes for a functional homologue of IL-10 (cmvIL-10, refs 10, 22). To evaluate the structure of UL111.5A-region transcripts expressed during latency we applied 3' RACE procedures and 5' primer walking RT-PCR to DNase-treated total RNA extracted from GM-Ps 14 days after infection with CMV strain Toledo (MOI=3).

For 3' RACE analysis, poly dT primed cDNA was subjected to two rounds of PCR amplification. In addition to amplifying the 3' end of the latency expressed transcript, PCR primers were designed to determine whether this transcript was spliced like that reported during productive infection. Thus, primers spanned across both intron 1 and intron 2. A single PCR product of approximately 600 bp was readily detected but no product was detected when template was omitted from the PCR reaction (FIG. 3). The PCR product was UA-cloned and the sequence determined from four individual clones. These clones all exhibited an identical sequence consistent with a single polyadenylation site 14 bp downstream of a consensus polyadenylation signal (AATAAA), indicating the same termination site as used during productive infection (AD169 nucleotide position 160430, accession number X17403). Sequencing of the four clones also revealed a processed transcript with a single spliced region of 76 bp which was identical to intron 1 of the transcript expressed during productive infection, but no other splicing was observed. The same 3' end and splicing pattern was observed in a further two replicate experiments using RNA from GM-P cultures latently infected with either strain Toledo or strain AD1 69 (data not shown). These experiments demonstrated that latent UL111.5A-region transcripts terminated at the same site reported for productive UL111.5A transcripts but differed with respect to intron 2 which remained unspliced during latency.

There are two previously identified transcriptional start sites within the region under examination. These are the start of the UL111.5A transcript at position 159642 (12) and the start of the UL111A transcript 27 bp upstream at position 159615 (1). Both transcripts encode ORFs which originate from the same methionine at position 159678. In the present invention, it was determined whether the UL111.5A-region transcripts expressed during latency were likely to utilise either of these transcription start sites by performing a series of primer walking RT-PCR reactions using the forward primers JAS-52 or JAS-53. Primer JAS-52 lies between the two start sites, with its 5' end at the UL111A start site and its 3' end 4 bp upstream of the UL111.5A start site. Primer JAS-53 lies upstream of both start sites, with its 3' end being 38 bp upstream of the UL111A start site. To determine whether latent transcripts initiated upstream of the UL111.5A start site, GM-P RNA was reverse transcribed and subjected to 40 cycles of PCR using cycle C parameters with primers JAS-52 and JAS-R5 followed by a second round of 25 cycles of PCR using cycle C parameters with primers JAS-52 and JAS-R4. Southern blot hybridisation revealed the presence a RT-dependent fragment that was smaller than a viral DNA template sized fragment and was consistent with a predicted 579 bp product derived from a single (intron 1) spliced transcript as detected during the 3' RACE mapping (FIG. 4A). No amplification was detected using mock infected GM-P RNA or when RNA was omitted from the reaction mixture. In addition to the 579 bp spliced transcript fragment, a genomic template sized fragment of 655 bp was also amplified from latently infected RNA. The DNase treatment of this sample, together with the dependence on RT suggests that this fragment was derived from an unspliced transcript. The amplification with forward primer JAS-52 of UL111.5A-region transcripts expressed during latent infection suggests that these transcripts initiate upstream of the start of the UL 111.5A transcript expressed during productive infection.

The RT-PCR was repeated with 40 cycles of amplification using cycle C parameters with primers JAS-53 and JAS-R5 followed by a second round of 25 cycles using cycle C parameters with primers JAS-53 and JAS-R4. A single, RT-dependent 712 bp product consistent with the amplification of an unspliced transcript was detected in infected GM-Ps (FIG. 4B). A spliced UL111.5A-region transcript was not detected and no products were amplified from mock infected GM-Ps or when RNA was omitted from the reaction. Comparable results were obtained when primer walking RT-PCR reactions using forward primers JAS-52 and JAS-53 were applied to DNase treated RNA extracted from GM-Ps latently infected with strain TowneVarRIT$_3$ (data not shown). Assuming binding of the full primer sequence is required for successful amplification, these data indicate that the spliced, latent UL111.5A-region transcript initiates within a 38 bp region (between nucleotide position 159577 and 159615) upstream of the productive UL111.5A start site which contains the UL111A start site (FIG. 5A). These data also suggest that an unspliced latent transcript utilises a different start site that is upstream of nucleotide position 159558.

In summary, structural analyses of UL111.5A-region transcripts expressed during latency revealed the presence of a novel transcript with a single intron and two exons that initiates within a small region upstream of UL111.5A start site and is co-terminal with UL111.5A transcripts expressed during productive infection. Sequence analysis of the spliced transcript using the National Centre for Biotechnology Information (NCBI) ORF Finder program revealed the presence of a single, 139 amino acid ORF. A BLAST search of the 139 amino acid sequence against the human genome demonstrated 27% identity and 46% similarity to human IL-10 over a 124 amino acid region (FIG. 6B). This 124 amino acid region is chosen since the BLAST search function provides an homology analysis over the longest stretch with any homology. It was concluded that a novel, spliced UL111.5A-region transcript expressed during latent infection encodes a putative cmvIL-10-like protein which is termed latency associated (LA)-cmvIL-10.

Example 7

Detection of UL111.5A Region Transcripts in Naturally Infected Individuals

Mononuclear cells were isolated from bone marrow (BM) and granulocyte-colony stimulating factor (G-CSF) mobilised peripheral blood (MPB) samples collected from healthy allograft donors. Total RNA was extracted from aliquots of $3.5 \times 10^5$–$1.0 \times 10^6$ cells and treated with RQ1 DNase to remove contaminating DNA before being subjected to RT-PCR. UL111.5A region transcripts were amplified for 40 cycles from random-primed cDNA using cycle A parameters with primers JAS-F1 and JAS-B1 followed by a second round of amplification for 35 cycles using cycle A parameters with primers JAS-F1 and JAS-R1. Products were resolved by gel electrophoresis before being transferred to nylon membranes and hybridised to an internal end-labelled oligonucleotide probe (JAS-R6). A 171 bp RT-dependent PCR fragment corresponding in size to spliced UL111.5A region transcripts was detected in two out of five BM donors and one out of eleven MPB donors (FIG. 6 and data not shown). No amplification was observed when RT or RNA was omitted from the reaction mixtures. The CMV serostatus of the donors was provided by Westmead Hospital. Out of the three UL111.5A transcript-positive donors, one was CMV seropositive and two were seronegative. It was concluded that the UL111.5A region was transcribed during natural latent CMV infection but that expression did not always correlate with donor serostatus.

Example 8

Discussion

This study reports the detection of transcription from the UL111.5A region of the human CMV genome during experimental latent infection of hematopoietic progenitor cells and in bone marrow and mobilized peripheral blood cells from naturally infected individuals. Although CMV encodes greater than 200 distinct genes, viral gene expression during the latent phase of infection remains poorly defined. To date, UL111.5A-region CMV latency associated transcripts (CLTs) and the previously identified MIE-region CLTs represent the only two classes of viral transcripts that have been detected during natural latent CMV infection and have been subjected to structural analyses. The detection of UL111.5A-region CLTs in GM-Ps latently infected with either CMV strain AD169, Towne or Toledo demonstrates that expression is strain independent and is a conserved feature of CMV. This is further supported by detection in naturally infected cell samples from healthy allograft donors, a finding consistent with a bone fide role for these transcripts during latency.

In terms of the function of UL111.5A-region CLTs the current analyses revealed a spliced transcript encoding a single, 139 amino acid ORF with homology to human IL-10. Human IL-10 is a multifunctional immunomodulatory cytokine that has potent immunosuppressive effects on hematopoietic cells (13). Its primary role is to suppress immune function by inhibiting the synthesis of pro-inflammatory cytokines such as IL-2, IFN-γ and TNF-α. IL-10 can also inhibit MHC class II and co-stimulatory adhesion molecule expression, resulting in the suppression of antigen specific T-cell proliferation.

The genomes of several herpesviruses including EBV (5, 14), equine herpesvirus 2 (18), human CMV (10, 12) and rhesus macaque, baboon and African green monkey CMVs (12) have regions with sequence homology to human IL-10. Several of these herpesviruses have been further shown to express a viral IL-10 homologue although these studies have been restricted to the productive phase of infection in permissive cells. This includes the viral IL-10 homologue encoded by human CMV, designated cmvIL-10, which is secreted by fibroblasts during productive infection (10) and has been subsequently demonstrated to function in a manner similar to human IL-10 (22).

In the present assessment of viral gene expression during latency, the 139 amino acid ORF was the only ORF identified on UL111.5A-region CLTs. The putative protein product, designated latency associated (LA)-cmvIL-10 is predicted to share the same initiation methionine as the cmvIL-10 expressed during productive CMV infection. In addition, like the processed UL111.5A transcript expressed during productive infection, splicing of the UL111.5A-region CLT (intron 1) maintains an ORF prior to the identified stop codon of UL111A. However, unlike the UL111.5A transcript, the UL111.5A-region CLT that we mapped does not contain a second intron, resulting in an in-frame stop codon at nucleotide position 160171. Thus, both LA-cmvIL-10 and cmvIL-10 are predicted to be co-linear for the first 127 amino acid, with divergent sequences for the remaining C-terminal portions.

The GM-P model of latency consistently results in >90% of cells harboring viral genomes (19). The disclosure herein demonstrates that approximately 1-6% of GM-Ps from latently infected cultures expressed detectable UL111.5A-region CLTs indicates a dissociation between transcription from this region and the presence of the viral genome, suggesting that latency may proceed in some cells that fail to express these transcripts. This finding is consistent with previous analyses which showed that MIE CLTs are expressed in approximately 2% of latently infected GM-Ps (7, 19). It remains to be determined whether MIE CLTs and UL111.5A-region CLTs are co-expressed in the same cells or whether they represent different populations of latently infected GM-Ps with potentially different biological functions.

In summary, the disclosure herein reports the first detection of gene expression from the UL111.5A region of the CMV genome during both experimental and natural latent infection. During latency, the virus expresses a novel, singly spliced transcript which is predicted to encode a protein (LA-cmvIL-10) with homology to human IL-10. Expression of LA-cmvIL-10 during the latent phase of infection is likely to contribute to the success of CMV as a human pathogen by suppression of the hosts ability to successfully mount an immune response against the virus in its latent form. The development of therapies to inhibit the ability of CMV to subvert the immune response during latency may ultimately lessen its ability to cause disease in allograft recipients.

Example 9

Compositions for Treatment

The suitable compounds and agents identified by the methods of the present invention which may be used for the treatment or prevention of disease states may be administered alone, although it is preferable that they be administered as a pharmaceutical composition.

In accordance with the best mode of performing the invention provided herein, specific preferred compositions are outlined below. The following are to be construed as merely illustrative examples of compositions and not as a limitation of the scope of the present invention in any way.

Example 9(a)

Composition for Parenteral Administration

A composition for intramuscular injection could be prepared to contain 1 mL sterile buffered water, and 1 mg of a suitable agent or compound.

Similarly, a composition for intravenous infusion may comprise 250 ml of sterile Ringer's solution, and 5 mg of a suitable agent or compound.

Example 9(b)

Injectable Parenteral Composition

A composition suitable for administration by injection may be prepared by mixing 1% by weight of a suitable agent or compound in 10% by volume propylene glycol and water. The solution is sterilized by filtration.

Example 9(c)

Capsule Composition

A composition of a suitable agent or compound in the form of a capsule may be prepared by filling a standard two-piece hard gelatin capsule with 50 mg of the agent or compound, in powdered form, 100 mg of lactose, 35 mg of talc and 10 mg of magnesium stearate.

Example 9(d)

Eye Drop Composition

A typical composition for delivery as an eye drop is outlined below:

| Suitable agent or compound | 0.3 g |
|---|---|
| Methyl Hydroxybenzoate | 0.005 g |
| Propyl Hydroxybenzoate | 0.06 g |
| Purified Water about to | 100.00 ml. |

The methyl and propyl hydroxybenzoates are dissolved in 70 ml purified water at 75° C., and the resulting solution is allowed to cool. The a suitable agent or compound is then added, and the solution sterilised by filtration through a membrane filter (0.22 μm pore size), and aseptically packed into sterile containers.

Example 9(e)

Composition for Inhalation Administration

For an aerosol container with a capacity of 20-30 ml: a mixture of 10 mg of a suitable agent or compound with 0.5-0.8% by weight of a lubricating agent, such as polysorbate 85 or oleic acid, is dispersed in a propellant, such as freon, and put into an appropriate aerosol container for either intranasal or oral inhalation administration.

Example 9(f)

Ointment Composition

A typical composition for delivery as an ointment includes 1.0 g of a suitable agent or compound, together with white soft paraffin to 100.0 g, dispersed to produce a smooth, homogeneous product.

Example 9(g)

Topical Cream Composition

A typical composition for delivery as a topical cream is outlined below:

| Suitable agent or compound | 1.0 g |
|---|---|
| Polawax GP 200 | 25.0 g |
| Lanolin Anhydrous | 3.0 g |
| White Beeswax | 4.5 g |
| Methyl hydroxybenzoate | 0.1 g |
| Deionised & sterilised Water to | 100.0 g |

The polawax, beeswax and lanolin are heated together at 60° C., a solution of methyl hydroxybenzoate is added and homogenisation achieved using high speed stirring. The temperature is then allowed to fall to 50° C. The agent or compound is then added and dispersed throughout, and the composition is allowed to cool with slow speed stirring.

Example 9(h)

Topical Lotion Composition

A typical composition for delivery as a topical lotion is outlined below:

| Suitable agent or compound | 1.2 g |
|---|---|
| Sorbitan Monolaurate | 0.8 g |
| Polysorbate 20 | 0.7 g |
| Cetostearyl Alcohol | 1.5 g |
| Glycerin | 7.0 g |
| Methyl Hydroxybenzoate | 0.4 g |
| Sterilised Water about to | 100.00 ml |

The methyl hydroxybenzoate and glycerin are dissolved in 70 ml of the water at 75° C. The sorbitan monolaurate, polysorbate 20 and cetostearyl alcohol are melted together at 75° C. and added to the aqueous solution. The resulting emulsion is homogenised, allowed to cool with continuous stirring and the agent or compound is added as a suspension in the remaining water. The whole suspension is stirred until homogenised.

REFERENCES

1. Chee, M. S., A. T. Bankier, S. Beck, R. Bohni, C. M. Brown, R. Cerny, T. Horsnell, C. A. Hutchison, 3rd, T. Kouzarides, and J. A. Martignetti. 1990. Analysis of the protein-coding content of the sequence of human cytomegalovirus strain AD169. Current Topics in Microbiology & Immunology 154:125-69.

2. Chevalier, M. S., G. M. Daniels, and D. C. Johnson. 2002. Binding of human cytomegalovirus US2 to major histocompatibility complex class I and II proteins is not sufficient for their degradation. Journal of Virology 76:8265-75.
3. Hahn, G., R. Jores, and E. S. Mocarski. 1998. Cytomegalovirus remains latent in a common precursor of dendritic and myeloid cells. Proceedings of the National Academy of Sciences of the United States of America 95:3937-42.
4. Hegde, N. R., R. A. Tomazin, T. W. Wisner, C. Dunn, J. M. Boname, D. M. Lewinsohn, and D. C. Johnson. 2002. Inhibition of HLA-DR assembly, transport, and loading by human cytomegalovirus glycoprotein US3: a novel mechanism for evading major histocompatibility complex class II antigen presentation. Journal of Virology 76:10929-41.
5. Hsu, D. H., R. de Waal Malefyt, D. F. Fiorentino, M. N. Dang, P. Vieira, J. de Vries, H. Spits, T. R. Mosmann, and K. W. Moore. 1990. Expression of interleukin-10 activity by Epstein-Barr virus protein BCRF1. Science 250:830-2.
6. Just, M., A. Buergin-Wolff, G. Emoedi, and R. Hernandez. 1975. Immunisation trials with live attenuated cytomegalovirus TOWNE 125. Infection 3:111-4.
7. Kondo, K., H. Kaneshima, and E. S. Mocarski. 1994. Human cytomegalovirus latent infection of granulocyte-macrophage progenitors. Proceedings of the National Academy of Sciences of the United States of America 91:11879-83.
8. Kondo, K., and E. S. Mocarski. 1995. Cytomegalovirus latency and latency-specific transcription in hematopoietic progenitors. Scandinavian Journal of Infectious Diseases—Supplement 99:63-7.
9. Kondo, K., J. Xu, and E. S. Mocarski. 1996. Human cytomegalovirus latent gene expression in granulocyte-macrophage progenitors in culture and in seropositive individuals. Proceedings of the National Academy of Sciences of the United States of America 93:11137-42.
10. Kotenko, S. V., S. Saccani, L. S. Izotova, O. V. Mirochnitchenko, and S. Pestka. 2000. Human cytomegalovirus harbors its own unique IL-10 homologue (cmvIL-10). Proceedings of the National Academy of Sciences of the United States of America 97:1695-700.
11. Larsson, S., C. Soderberg-Naucler, F. Z. Wang, and E. Moller. 1998. Cytomegalovirus DNA can be detected in peripheral blood mononuclear cells from all seropositive and most seronegative healthy blood donors over time. Transfusion 38:271-8.
12. Lockridge, K. M., S. S. Zhou, R. H. Kravitz, J. L. Johnson, E. T. Sawai, E. L. Blewett, and P. A. Barry. 2000. Primate cytomegaloviruses encode and express an IL-10-like protein. Virology 268:272-80.
13. Moore, K. W., R. de Waal Malefyt, R. L. Coffman, and A. O'Garra. 2001. Interleukin-10 and the interleukin-10 receptor. Annual Review of Immunology 19:683-765.
14. Moore, K. W., P. Vieira, D. F. Fiorentino, M. L. Trounstine, T. A. Khan, and T. R. Mosmann. 1990. Homology of cytokine synthesis inhibitory factor (IL-10) to the Epstein-Barr virus gene BCRFI.[erratum appears in Science 1990 October 26; 250(4980):494]. Science 248:1230-4.
15. Plotkin, S. A., T. Furukawa, N. Zygraich, and C. Huygelen. 1975. Candidate cytomegalovirus strain for human vaccination. Infection & Immunity 12:521-7.
16. Quinnan, G. V., Jr., M. Delery, A. H. Rook, W. R. Frederick, J. S. Epstein, J. F. Manischewitz, L. Jackson, K. M. Ramsey, K. Mittal, and S. A. Plotkin. 1984. Comparative virulence and immunogenicity of the Towne strain and a nonattenuated strain of cytomegalovirus. Annals of Internal Medicine 101:478-83.
17. Rawlinson, W. D., and B. G. Barrell. 1993. Spliced transcripts of human cytomegalovirus. Journal of Virology 67:5502-13.
18. Rode, H. J., W. Janssen, A. Rosen-Wolff, J. J. Bugert, P. Thein, Y. Becker, and G. Darai. 1993. The genome of equine herpesvirus type 2 harbors an interleukin 10 (IL10)-like gene. Virus Genes 7:111-6.
19. Slobedman, B., and E. S. Mocarski. 1999. Quantitative analysis of latent human cytomegalovirus. Journal of Virology 73:4806-12.
20. Smith, K. L., J. K Kulski, T. Cobain, and R. A. Dunstan. 1993. Detection of cytomegalovirus in blood donors by the polymerase chain reaction. Transfusion 33:497-503.
21. Soderberg-Naucler, C., K. N. Fish, and J. A. Nelson. 1997. Reactivation of latent human cytomegalovirus by allogeneic stimulation of blood cells from healthy donors. Cell 91:119-26.
22. Spencer, J. V., K. M. Lockridge, P. A. Barry, G. Lin, M. Tsang, M. E. Penfold, and T. J. Schall. 2002. Potent immunosuppressive activities of cytomegalovirus-encoded interleukin-10.[erratum appears in J Virol 2002 April; 76(7):3585]. Journal of Virology 76:1285-92.
23. Tomazin, R., J. Boname, N. R. Hegde, D. M. Lewinsohn, Y. Altschuler, T. R. Jones, P. Cresswell, J. A. Nelson, S. R. Riddell, and D. C. Johnson. 1999. Cytomegalovirus US2 destroys two components of the MHC class II pathway, preventing recognition by CD4+ T cells. Nature Medicine 5:1039-43.

The invention claimed is:

1. An isolated nucleic acid comprising a continuous sequence as defined in SEQ ID NO:1 or a fragment thereof, wherein the fragment is less than 150 nucleotides in length and comprises SEQ ID NO: 4 and SEQ ID NO: 9.

2. A vector comprising a nucleic acid according to claim 1.

3. A recombinant host cell comprising the vector in accordance with claim 2.

4. A recombinant host cell according to claim 3, wherein the vector expresses a polypeptide comprising a sequence as defined in SEQ ID NO: 10.

5. A kit comprising the isolated nucleic acid as set forth in claim 1 and reagents for detecting hybridization of said nucleic acid.

6. A method for screening a subject for infection by a virus of the herpesvirideae group, the method comprising:
(a) obtaining a biological sample from said subject;
(b) contacting said biological sample from said subject with an isolated nucleic acid of claim 1; and
(c) detecting the presence or absence of hybridization between a nucleic acid in said biological sample and the isolated nucleic acid of claim 1, wherein the presence of hybridization indicates infection.

7. The method of claim 6, wherein the isolated nucleic acid is capable of selectively hybridizing to a nucleic acid encoding an IL-10 homologue expressed during the latent phase of infection by a virus of the herpesvirideae group.

8. A method of diagnosing infection or lack of infection of a subject by a virus of the herpesvirideae group, the method comprising:
(a) obtaining a biological sample from said subject;
(b) contacting said biological sample from said subject with the isolated nucleic acid of claim 1;
(c) detecting the presence or absence of hybridization between a nucleic acid in said biological sample and the isolated nucleic acid of claim 1, and
(d) diagnosing infection of said subject based on the presence of said hybridization or diagnosing lack of infection based on the absence of said hybridization.

9. The isolated nucleic acid of claim 1, wherein said nucleic acid consists of said sequence as defined in SEQ ID NO: 1 or a fragment thereof that is less than 150 nucleotides in length and comprises SEQ ID NO: 4 and SEQ ID NO: 9.

10. A method of diagnosis of a latent infection by a virus of the herpesvirideae group in a subject, the method comprising:
(a) obtaining a biological sample from said subject; and
(b) detecting the presence or absence of a nucleic acid according to claim 1 in the sample, wherein detection of said nucleic acid is diagnostic of said latent infection.

11. The method of claim 10, wherein said detecting is performed by polymerase chain reaction utilizing a nucleic acid as defined in SEQ ID NO: 4 in combination with a nucleic acid fragment as defined in any one of SEQ ID NOs: 5-9.

* * * * *

SEQUENCE LISTING

```
<160> NUMBER OF SEQ ID NOS: 10

<210> SEQ ID NO 1
<211> LENGTH: 749
<212> TYPE: DNA
<213> ORGANISM: Cytomegalovirus
<220> FEATURE:
<221> NAME/KEY: VARIANT
<222> LOCATION: 744
<223> OTHER INFORMATION: r = g or a
<220> FEATURE:
<221> NAME/KEY: VARIANT
<222> LOCATION: 745
<223> OTHER INFORMATION: b = g, c or t
<220> FEATURE:
<221> NAME/KEY: VARIANT
<222> LOCATION: 746
```

```
<223> OTHER INFORMATION: m = a or c
<220> FEATURE:
<221> NAME/KEY: VARIANT
<222> LOCATION: 747
<223> OTHER INFORMATION: d = a, g or t
<220> FEATURE:
<221> NAME/KEY: VARIANT
<222> LOCATION: 749
<223> OTHER INFORMATION: n = a, t, c, or g

<400> SEQUENCE: 1
cataaaggac cacctacctg ggacgcgcag ttgggcggcg gactgggacg gcatgctgcg      60
gtgatgctgt cggtgatggt ctcttcctct ctggtcctga tcgtcttttt tctaggcgct     120
tccgaggagg cgaagccggc gacgacgacg acgataaaga atacaaagcc gcagtgtcgt     180
ccagaggatt acgcgaccag attgcaagat ctccgcgtca cctttcatcg agtaaaacct     240
acgttgcaac gtgaggacga ctactccgtg tggctcgacg gtacggtggt caaaggctgt     300
tggggatgca gcgtcatgga ctggttgttg aggcggtatc tggagatcgt gttccccgca     360
ggcgaccacg tctatcccgg actcaagacg gaattgcata gtatgcgctc gacgctagaa     420
tccatctaca aagacatgcg gcaatgcgta agtgtctctg tggcggcgct gtccgcacag     480
aggtaacaac gtgttcatag cacgctgttt tacttttgtc gggctcccag cctctgttag     540
gttgcggaga taagtccgtg attagtcggc tgtctcagga ggcggaaagg aaatcggata     600
acggcacgcg gaaaggtctc agcgagttgg acacgttgtt tagccgtctc gaagagtatc     660
tgcactcgag aaagtagcgt tgcgatttgc agtccgctcc ggtgtcgttc acccagttac     720
tttaataaac gtactgttta accrbmdcn                                      749

<210> SEQ ID NO 2
<211> LENGTH: 19
<212> TYPE: DNA
<213> ORGANISM: Cytomegalovirus

<400> SEQUENCE: 2
actattctaa ccgcggaag                                                  19

<210> SEQ ID NO 3
<211> LENGTH: 23
<212> TYPE: DNA
<213> ORGANISM: Cytomegalovirus

<400> SEQUENCE: 3
cataaaggac cacctacctg gga                                             23

<210> SEQ ID NO 4
<211> LENGTH: 32
<212> TYPE: DNA
<213> ORGANISM: Cytomegalovirus

<400> SEQUENCE: 4
tacaaagccg cagtgtcgtc cagaggatta cg                                   32

<210> SEQ ID NO 5
<211> LENGTH: 26
<212> TYPE: DNA
<213> ORGANISM: Cytomegalovirus

<400> SEQUENCE: 5
caacaaccag tccatgacgc tgcatc                                          26

<210> SEQ ID NO 6
```

```
<211> LENGTH: 27
<212> TYPE: DNA
<213> ORGANISM: Cytomegalovirus

<400> SEQUENCE: 6
gtagatggat tctagcgtcg agcgcat                                            27

<210> SEQ ID NO 7
<211> LENGTH: 27
<212> TYPE: DNA
<213> ORGANISM: Cytomegalovirus

<400> SEQUENCE: 7
tcctgagaca gccgactaat cacggac                                            27

<210> SEQ ID NO 8
<211> LENGTH: 28
<212> TYPE: DNA
<213> ORGANISM: Cytomegalovirus

<400> SEQUENCE: 8
tctcgagtgc agatactctt cgagacgg                                           28

<210> SEQ ID NO 9
<211> LENGTH: 28
<212> TYPE: DNA
<213> ORGANISM: Cytomegalovirus

<400> SEQUENCE: 9
gaccaccgta ccgtcgagcc acacggag                                           28

<210> SEQ ID NO 10
<211> LENGTH: 139
<212> TYPE: PRT
<213> ORGANISM: Cytomegalovirus

<400> SEQUENCE: 10

Met Leu Ser Val Met Val Ser Ser Leu Val Leu Ile Val Phe Phe
 1               5                  10                  15

Leu Gly Ala Ser Glu Glu Ala Lys Pro Ala Thr Thr Thr Ile Lys Asn
                20                  25                  30

Thr Lys Pro Gln Cys Arg Pro Glu Asp Tyr Ala Thr Arg Leu Gln Asp
         35                  40                  45

Leu Arg Val Thr Phe His Arg Val Lys Pro Thr Leu Gln Arg Glu Asp
     50                  55                  60

Asp Tyr Ser Val Trp Leu Asp Gly Thr Val Val Lys Gly Cys Trp Gly
 65                  70                  75                  80

Cys Ser Val Met Asp Trp Leu Leu Arg Arg Tyr Leu Glu Ile Val Phe
                 85                  90                  95

Pro Ala Gly Asp His Val Tyr Pro Gly Leu Lys Thr Glu Leu His Ser
            100                 105                 110

Met Arg Ser Thr Leu Glu Ser Ile Tyr Lys Asp Met Arg Gln Cys Val
        115                 120                 125

Ser Val Ser Val Ala Ala Leu Ser Ala Gln Arg
    130                 135
```